US006316616B1

(12) United States Patent
Jacobsen et al.

(10) Patent No.: US 6,316,616 B1
(45) Date of Patent: Nov. 13, 2001

(54) PARALLEL COMBINATORIAL APPROACH TO THE DISCOVERY AND OPTIMIZATION OF CATALYSTS AND USES THEREOF

(75) Inventors: Eric N. Jacobsen, Boston; Matthew S. Sigman, Somerville, both of MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 09/064,462

(22) Filed: Apr. 22, 1998

Related U.S. Application Data

(60) Provisional application No. 60/080,461, filed on Apr. 2, 1998.

(51) Int. Cl.[7] .......................... B01J 31/02; C07C 69/017; C07C 275/18; C07D 223/12
(52) U.S. Cl. .......................... 540/484; 502/200; 502/172; 540/484; 546/224; 548/336.1; 548/557; 548/537; 560/103; 560/138; 564/27; 564/56
(58) Field of Search .................... 548/336.1, 557, 548/537; 560/138, 103; 564/27, 56; 540/484; 546/224; 502/172, 200

(56) References Cited

U.S. PATENT DOCUMENTS

| | | |
|---|---|---|
| 5,500,807 | 3/1996 | Lavin et al. . |
| 5,525,735 | 6/1996 | Gallop et al. . |
| 5,545,568 | 8/1996 | Ellman . |
| 5,573,905 | 11/1996 | Lerner et al. . |
| 5,582,997 | 12/1996 | Blondelle et al. . |
| 5,593,853 | 1/1997 | Chen et al. . |
| 5,599,538 | 2/1997 | Paul et al. . |
| 5,637,459 | 6/1997 | Burke et al. . |
| 5,650,489 | 7/1997 | Lam et al. . |
| 5,723,598 | 3/1998 | Lerner et al. . |
| 5,773,598 | 6/1998 | Burke et al. . |

FOREIGN PATENT DOCUMENTS

WO 98/03521   1/1998   (WO) .

OTHER PUBLICATIONS

Borman Stu, "Combinatorial Catalysts : Methods devised to create arrays of catalysts to screen for enantioselective activity", Chemical and Engineering News, vol. 74, No. 45 pp. 37–39 (Nov. 4, 1996).

Francis B. M. and Jacobsen N. E., "Discovery of Novel Catalysts for Alkene Epoxidation from Metal–Binding Combinatorial Libraries", Angewandte Chemie Int. Ed. Engl. vol. 38 No. 7 : 937–941 (Apr. 1, 1999).

Gennari et al., "Combinatorial Libraries: Studies in Molecular Recognition and the Quest for New Catalysts", Liebigs Annalen/Recueil pp. 637–647 (1997).

Bousquet, C. et al., "Auxiliaires Cétoniques Chiraux dans la Synthèse Asymétrique des α–Aminoacides Selon Strecker," *Bull Soc. Chim. Fr.* pp. 513–520, 130, 1993.

Burgess, K., et al., "New Catalysts and Conditions for a C–H Insertion Reaction Identified by High Throughput Catalyst Screening," *Angew. Chem. Int. Ed. Engl.*, 35, No. 2, pp. 220–222, 1996.

Cogan, D., et al., "Catalytic Asymmetric Oxidation of tert––Butyl Disulfide. Synthesis of tert–Butanesulfinamides, tert–Butyl Solfoxides, and tert–Butanesulfinimines," *Journal of the American Chemical Society*, vol. 120, No. 32, Aug. 19, 1998.

Cole, B., et al., "Discovery of Chiral Catalysis through Ligand Diversity: Ti–Catalyzed Enantioselective Addition of TMSCN to meso Epoxides," *Angew. Chem. Int. Ed. Engl.*, 35, No. 15, pp. 1668–1671, 1996.

Fadel, A., et al., "A Straightforward Synthesis of Both Enantiomers of Allo–Norcoronamic Acids and Allo–Coronamic Acids, by Asymmetric Strecker Reaction from Alkylcyclopropanone Acetals," *Tetrahedron: Asymmetry 9* pp. 305–320, 1998.

Harada, K., et al., "Sterically Controlled Syntheses of Optically Active Organic Compounds. XIX. Asymmetric Syntheses of Amino Acids by the Strecker Reaction," *Bulletin of the Chemical Society of Japan*, vol. 46, pp. 1865–1868, 1973.

Heine, A., et al., "An Antibody exo Diels–Alderase Inhibitor Complex at 1.95 Angstrom Resolution,"+01 *Science*, vol. 279, Mar. 20, 1998.

Kunz, H., et al., "Stereoselective Synthesis of $_L$–Amino Acids via Strecker and Ugi Reaktions on Carbohydrate Templates," *Synthesis*, pp. 1039–1042, Nov. 1991.

Kunz, H., et al., "Reversal of Asymmetric Induction in Stereoselective Strecker Synthesis on Galactosyl Amine as the Chiral Matrix," *Tetrahedron Letters*, vol. 29, No. 35, pp. 4397–4400, 1988.

Nakamura, H., et al., "Catalytic Asymmetric Allylation of imines via Chiral Bis–$_{TT}$–allylpalladium Complexes," *J. Am. Chem. Soc.*, 102, pp. 4242–4243, 1998.

Reetz, M., et al., "Creation of Enantioselective Biocatalysts for Organic Chemistry by In Vitro Evolution," *Angew. Chem. Int. Ed. Engl.*, 36, No. 24, pp. 2830–2832, 1997.

(List continued on next page.)

*Primary Examiner*—Joseph K. McKane
*Assistant Examiner*—Sonya N. Wright
(74) *Attorney, Agent, or Firm*—Dana M. Gordon; Foley Hoag & Eliot LLP

(57) ABSTRACT

The present invention provides methods and compositions, i.e. synthetic libraries of candidate compounds, useful in the discovery and optimization of compounds which catalyze at least one chemical transformation. In certain instances, the subject compounds catalyze a chemoselective, regioselective, stereoselective or enantioselective transformation.

13 Claims, 5 Drawing Sheets

OTHER PUBLICATIONS

Romesberg, F., et al., "Immunological Origins of Binding and Catalysis in a Diels–Alderase Antibody," *Science*, vol. 279, pp. 1929–1933, Mar. 20, 1998.

Sigman, M.S., et al., "Schiff Base Catalysts for the Asymmetric Strecker Reaction Identified and Optimized from Parallel Synthetic Libraries," *J. Am. Chem. Soc.*, 120, pp. 4901–4902, 1998.

Stout, D.M., et al., "Asymmetric Strecker Synthesis: Isolation of Pure Enantiomers and Mechanistic Implications," *J. Org. Chem.*, 48, pp. 5369–5373, 1983.

Tan, D., et al., "Stereoselective Synthesis of over Two Million Compounds Having Structural Feature Both Reminiscent of Natural Products and Compatible with Miniaturized Cell–Based Assays," *J. Am. Chem. Soc.*, 120, pp. 8565–8566, 1998.

Taylor, S., et al., Thermographic Selection of Effective Catalysts from an Encoded Polymer–Bound Library, *Science*, vol. 280, pp. 267–270, Apr. 10, 1998.

Weinges, K., et al., "Über Die Asymmetrische Strecker–Synthese mit (S)–(–)–1–Phenylethylamin als Chiralem Hilfsreagens," *Chem. Ber. 110*, pp. 2098–2105, 1977.

Weinges, K., et al., "Die Asymmetrische Strecker–Synthese von Aliphatischen α–Methyl–α–Aminosäuren," *Chem. Ber. 106*, pp. 2291–2297, 1973.

Yuasa, Y., et al., "An Improved Synthesis of (S)–Aspartyl–(7,7–Dimenthyl–norborn–2R–yl)–(S)–Alanine Methyl Ester, A New High Intensity Artificial Sweetner", *Tetrahedron*, vol. 48, No. 17, pp. 3473–3484, 1992.

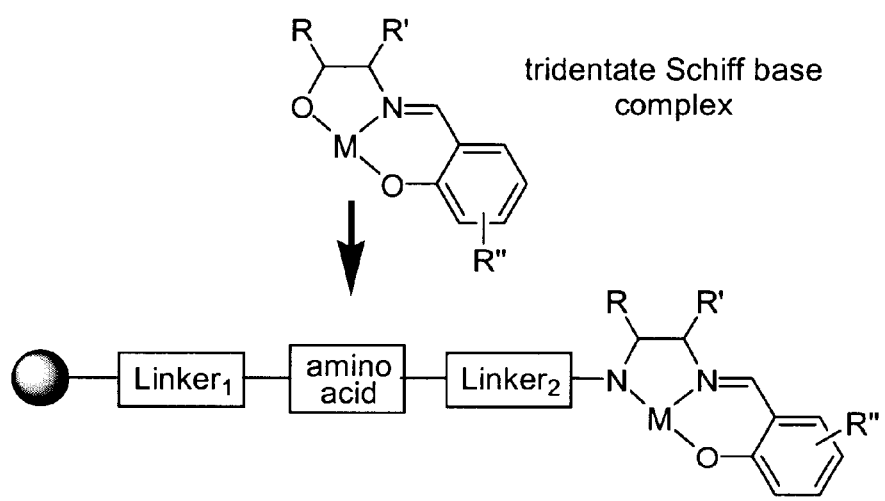
Figure 1. Generalized Structure of a Potential Catalyst System.

Figure 2. Variegated Libraries 1-3.

Library 1

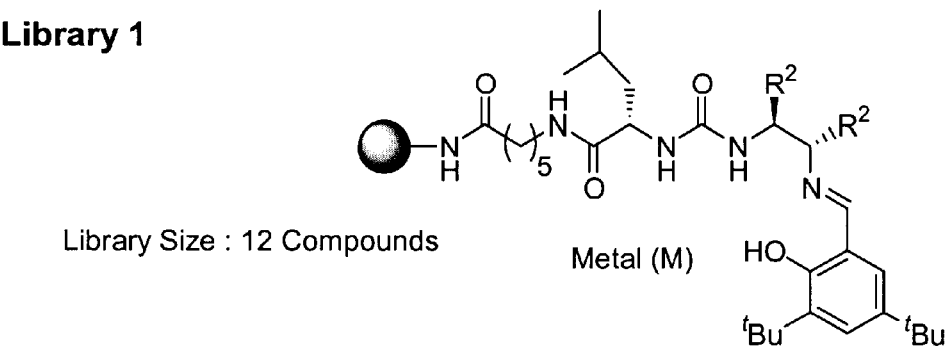

Library Size : 12 Compounds     Metal (M)

| M | None | Ti | Mn | Fe | Ru | Co | Cu | Zn | Gd | Nd | Yb | Eu |
|---|------|----|----|----|----|----|----|----|----|----|----|-----|
| ee (%) | 19 | 4 | 5 | 10 | 13 | 0 | 9 | 1 | 2 | 3 | 0 | 5 |
| conv.(%) | 59 | 30 | 61 | 69 | 63 | 68 | 55 | 91 | 95 | 84 | 94 | 34 |

Library 2

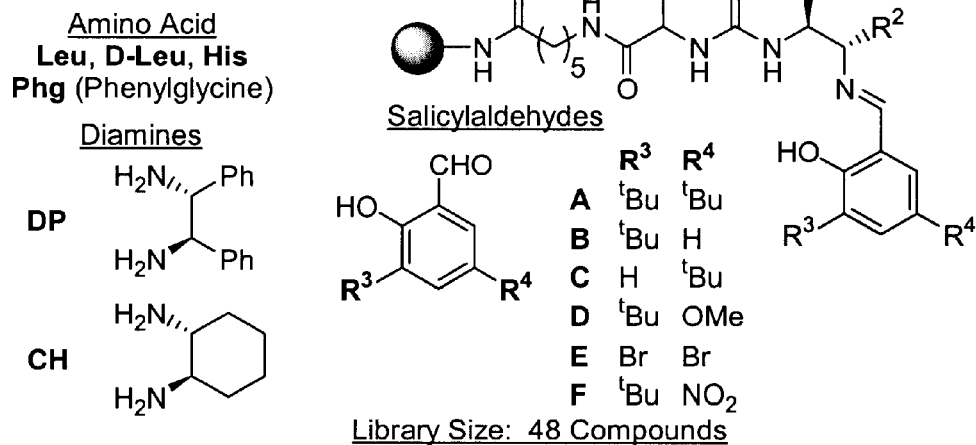

Amino Acid
**Leu, D-Leu, His
Phg** (Phenylglycine)

Diamines

DP

CH

Salicylaldehydes

|   | $R^3$ | $R^4$ |
|---|-------|-------|
| A | $^t$Bu | $^t$Bu |
| B | $^t$Bu | H |
| C | H | $^t$Bu |
| D | $^t$Bu | OMe |
| E | Br | Br |
| F | $^t$Bu | $NO_2$ |

Library Size: 48 Compounds

Library 3

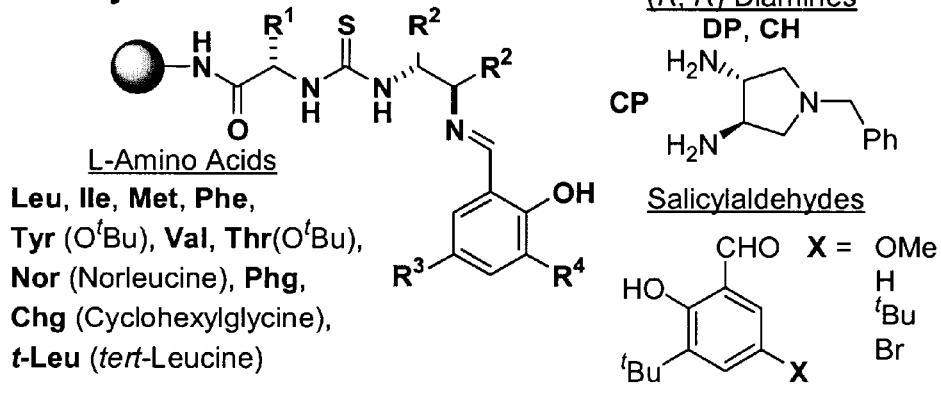

L-Amino Acids
**Leu, Ile, Met, Phe,
Tyr ($O^t$Bu), Val, Thr**($O^t$Bu),
Nor (Norleucine), **Phg,
Chg** (Cyclohexylglycine),
t-Leu (tert-Leucine)

(R, R)-Diamines
DP, CH

CP

Salicylaldehydes

X = OMe
H
$^t$Bu
Br

Library Size: 132 Compounds

Figure 3. Enantioselectivity in the Catalyzed Strecker Reaction as a Function of Metal-Free Catalyst Utilized.
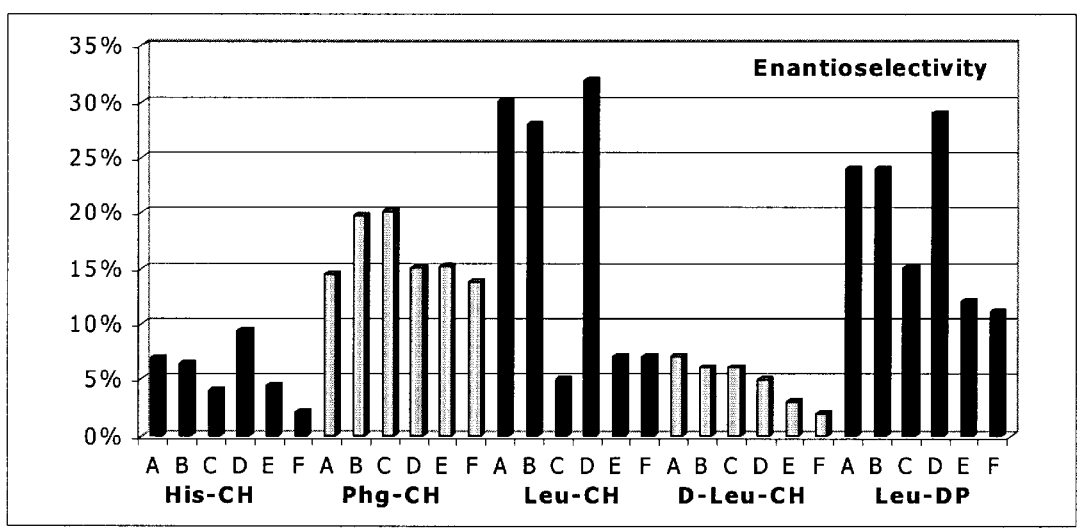

Figure 4. Enantioselectivities Observed in the Catalyzed Strecker Reaction Utilizing Members of Library 3.
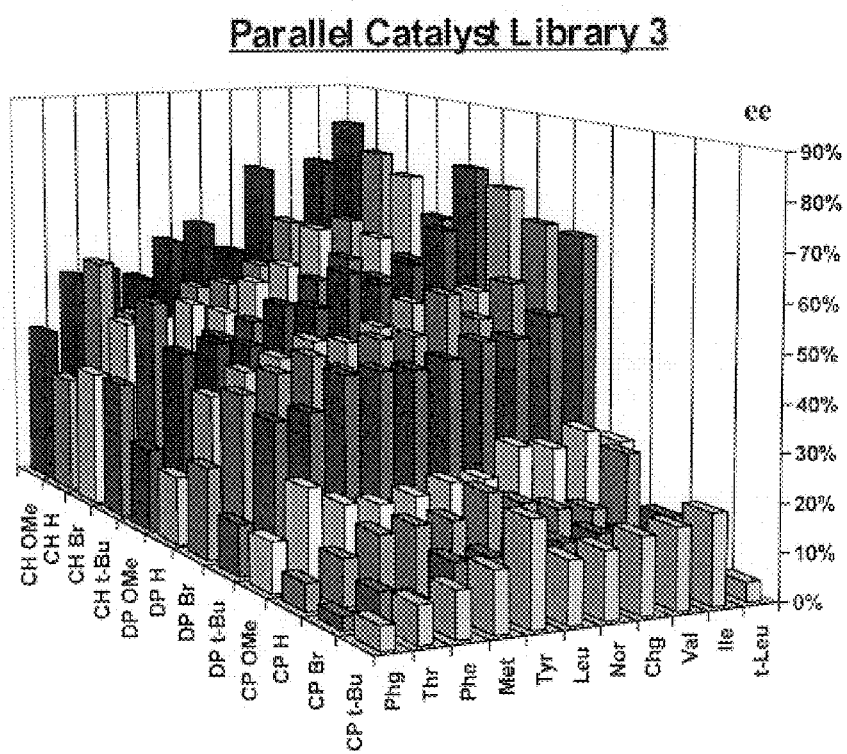

PARALLEL COMBINATORIAL APPROACH TO THE DISCOVERY AND OPTIMIZATION OF CATALYSTS AND USES THEREOF

RELATED APPLICATIONS

The present application claims priority to United States Provisional Patent Application No. 60/080,461, filed Apr. 2, 1998, the entire contents of which are hereby incorporated by reference.

BACKGROUND OF THE INVENTION

During the course of a chemical reaction, the reactants may undergo a series of transformations comprising passing through transition states (local energy maxima) and intermediates (local energy minima) until the products are formed. In molecular terms, these transformations reflect changes in bond lengths, angles, etc. The evolution from reactants to products, in a reaction that does not pass through any intermediates, may be viewed simply as involving formation of a transition state which decomposes to yield the products. The overall rate of this simple reaction can be expressed in terms of the equilibrium constants characterizing the equilibria between the reactants, the transition state, and the products.

Under these circumstances, catalysis can be regarded as a stabilization of the transition state for the reaction. A catalyst is a substance that increases the rate of a reaction, by lowering the energy of the transition state, and is recovered substantially unchanged at the end of the reaction. Although the catalyst is not consumed, it is agreed that the catalyst participates in the reaction. Despite the commercial importance of catalysis, major limitations are associated with both enzymatic and non-enzymatic catalysis. Economically-viable, efficient, and reliable transition metal-catalyzed processes are relatively few in number. The industrial utility of such processes may be diminished by their high operating costs, the incompatibility of the requisite reagents with environmental or toxicological imperatives, or difficulties associated with the isolation and purification of the desired products. Furthermore, non-enzymatic catalysts are not yet known for many important chemical reactions. Enzymatic catalysis depends on the existence and discovery of naturally occurring enzymes with the appropriate specificity and catalytic function to perform a particular reaction. Enzymes are not known for many, if not most, chemical transformations.

The immune system has been shown to have the ability to generate various de novo antibody catalysts. In short, antibodies are elicited to a hapten designed to mimic the transition state of the reaction of interest; the resulting antibodies are then screened for catalytic activity. Advances in the design of transition state analogues, and in the methods of generation and screening of antibodies to those analogues have resulted in catalytic antibodies for a wide range of chemical transformations (cf. inter alia: Romesberg et al. *Science* 1998, 279, 1929–1933; Heine et al. *Science* 1998, 279, 1934–1940; and references therein). Of course, an approach to catalysis based upon catalytic antibodies is limited in scope. First, this approach presupposes a knowledge of the transition state for a transformation. Second, it may be difficult or impossible to synthesize the required transition state analogue(s). Finally, antibodies are proteins and are subject to the limitations associated with polypeptides, e.g. susceptibility to proteolytic degradation, high molecular weight, and poor solubility characteristics.

The present invention overcomes the aforementioned limitations by providing a novel approach to the discovery and optimization of new catalysts. The invention provides a parallel combinatorial method for the preparation, evaluation, and optimization of organic molecules as convenient, readily obtainable and inexpensive catalysts possessing a high degree of specificity and efficiency. In certain embodiments, catalysts that do not rely on a transition metal ion for activity are provided. In other embodiments, this invention is useful in increasing the rate of chemical reactions which can also be catalyzed by enzymes such as oxidoreductases, transferases, hydrolases, lyases, isomerases and ligases. In certain embodiments, this invention is useful in increasing the rate of chemical reactions for which no catalysts, either enzymatic or non-enzymatic, are known presently. Such reactions include, among others, oxidations, reductions, additions, condensations, eliminations, substitutions, cleavages, rearrangements, and kinetic resolutions.

In accordance with this invention, the subject catalysts may increase the rate of a chemical reaction by more than a factor of one hundred, preferably more than a factor of one thousand, and most preferably more than a factor of ten thousand.

Furthermore, research into the relationship between catalyst structure and catalytic properties is a central theme in such active and disparate fields as asymmetric synthesis, medicinal chemistry, process chemistry, selective catalysis, bioremediation, sensor discovery and development, bioorganic chemistry, and bioinorganic chemistry. The numerous advances made recently in these fields underscore the utility of catalysts with well-defined structural, electronic and/or stereochemical features. However, the de novo rational design of such catalysts remains extremely challenging, if not unattainable at present, especially if novel physical and chemical properties are sought. In this context, a systematic method for the expedient generation of new classes of catalysts will be of great value.

Immobilization, or isolation within a semi-permeable membrane, of a catalyst would enable the reuse of a catalyst without the need for tedious isolation and purification protocols; additionally, this approach may help avoid the common problems of gradual degradation and/or fouling of catalysts. In this regard, Kobayashi and Nagayama recently disclosed the development of immobilized, microencapsulated Lewis acid catalysts that are both recoverable and reusable (*J. Am. Chem. Soc.* 1998, 120, 2985). Furthermore, these researchers found that in some cases the activity of the encapsulated catalysts is even greater than that of the non-encapsulated catalysts. Examples of the activity and reuse of enzymes contained within semi-permeable membranes have been reported by Whitesides, Bednarski, and others. The catalysts of the present invention may be immobilized and/or isolated within semi-permeable membranes and used as such.

SUMMARY OF THE INVENTION

The present invention provides methods and compositions, i.e. synthetic libraries of compounds, for identifying novel compounds which catalyze at least one chemical transformation. The subject method comprises: (a) chemically synthesizing a variegated library of candidate catalysts; and (b) screening the library of candidate catalysts to isolate/identify those members that catalyze a given reaction. Utilizing the techniques of combinatorial chemistry, e.g., direct characterization, encoding, spatially addressing and/or deconvolution, the molecular identity of individual members of the library of candidate catalysts can be ascertained in a screening format. Another aspect of the present invention pertains to kits for carrying out the instant method. Still another aspect of the present invention provides compositions including one or more of the catalysts identified by the instant method.

BRIEF DESCRIPTION OF THE FIGURES

FIG. 1 depicts a generalized structure of a potential catalyst system.

FIG. 2 depicts the structures of the members of Libraries 1–3.

FIG. 3 depicts the enantioselectivities observed in the catalyzed Strecker reaction as a function of the structure of the metal-free catalyst utilized.

FIG. 4 depicts the enantioselectivities observed in the catalyzed Strecker reaction utilizing members of Library 3.

DETAILED DESCRIPTION OF THE INVENTION

Figure 5:
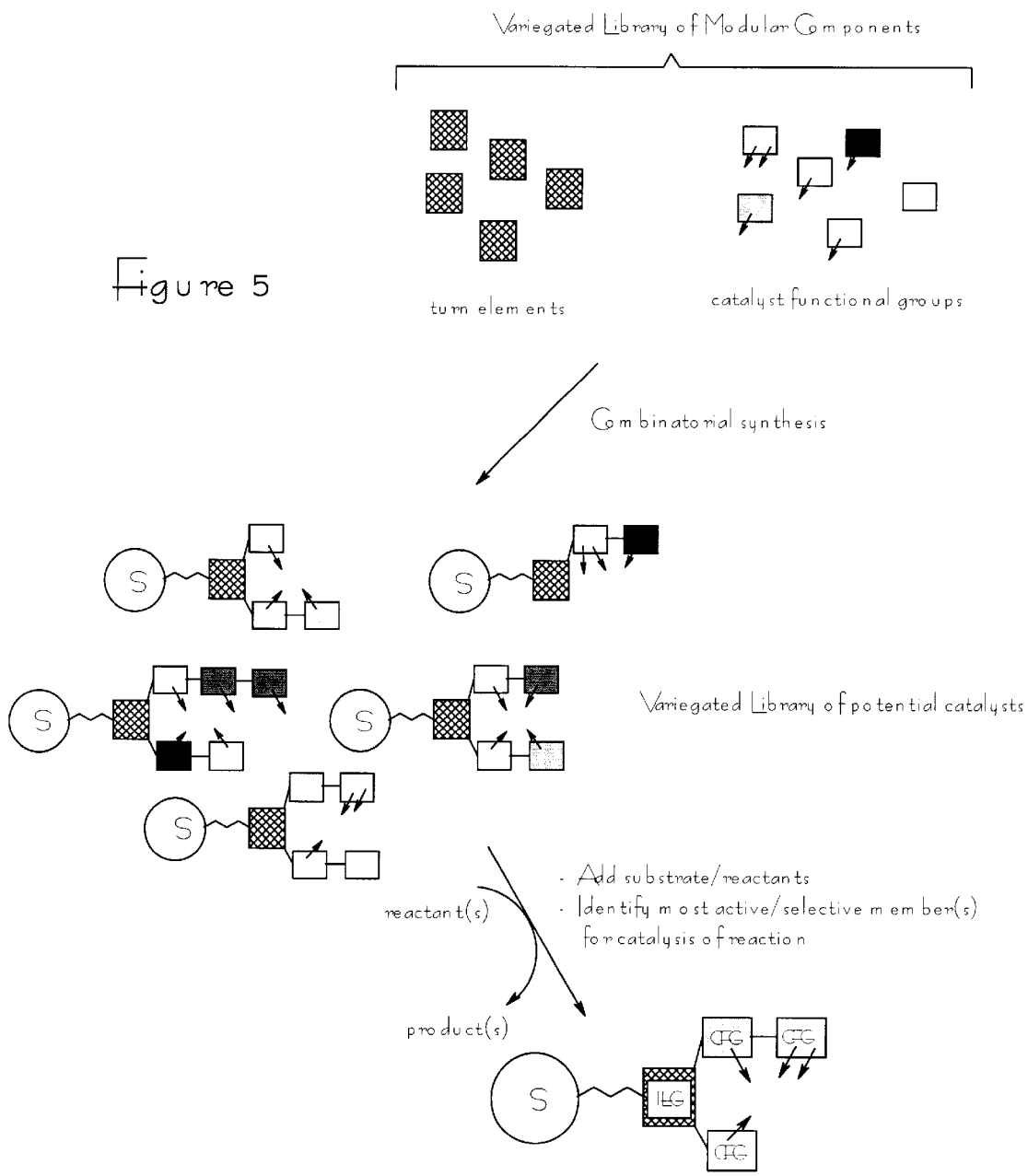
FIG. 5 depicts schematically a combinatorial strategy for the generation of libraries of potential catalysts.

The synthesis and screening of combinatorial libraries is a validated strategy for the identification and study of ligand-receptor interactions. For recent reviews on strategies for the synthesis of small-molecule libraries, see: Thompson et al. (1996) *Chem Rev.* 96:555; Armstrong et al. (1996) *Acc. Chem. Res.* 29:123; Gordon et al. (1994) *J. Med. Chem.* 37:1385. For combinatorial approaches to the study of ligand-receptor interactions, see Still et al. (1996) *Acc. Chem. Res.* 29:155, and references therein; Yu et al. (1994) *Cell* 76:933; Combs et al. (1996) *J. Am. Chem. Soc.* 118:287; Zuckermann et al. (1994) *J. Med. Chem.* 37:2678; Wang et al. (1995) *J. Med. Chem.* 38:2995; Campbell et al. (1995) *J. Am. Chem. Soc.* 117:5381. In this context, combinatorial systems have allowed many structural changes to be examined simultaneously, thus allowing an evaluation of, for example, synergistic effects in recognition events. Since the stability of a transition state-catalyst complex is similarly dependent on numerous interrelated variables, including but limited to the steric and electronic characteristics of the catalyst and substrate, combinatorial chemistry could also provide a powerful approach for discovering new classes of catalysts, and/or new members of known classes of catalysts. For example, spatially addressed synthetic libraries have been applied with success for the identification of selective catalysts (Burgess et al. (1996) *Angew. Chem. Int. Ed. Engl.* 35:220; and Reetz et al. (1997) *Angew. Chem. Int. Ed. Engl.* 36:2830).

I. Overview.

The method of the present invention is a fundamentally different approach, based on parallel combinatorial synthesis schemes, to discovering and optimizing catalysts for chemical transformations. Rather than begin with a predefined catalytic structure, the subject method involves the generation of libraries of potential catalysts from diverse sets of functional groups and conformational restrictions; this approach results in a wide range of potentially catalytic environments. As described below, we have demonstrated that the subject combinatorial libraries can be successfully applied to the identification and optimization of novel catalysts, e.g. for the addition of nucleophiles to π-bonds. Moreover, the structural features that lead to catalysis, and selectivity where relevant, are quite unanticipated, and comprise non-intuitive synergistic effects between structural elements of the catalysts.

In its most general embodiment, the process of the present method comprises: (a) the chemical synthesis of a variegated library of potential catalysts from an assortment of structural elements comprising various functional groups and turn elements; and (b) screening the library of catalysts to identify/isolate those members that catalyze a given transformation. Through the application of the techniques of combinatorial chemistry, e.g., encoding, spatially addressing, mass spectroscopy and/or deconvolution, libraries of potential catalysts can be synthesized by batch processes and, perhaps more importantly, the molecular identity of the individual members of the library can be ascertained in a screening format. It will be understood that once a library of potential catalysts is constructed, the library can be screened for catalytic activity in any number of chemical transformations.

Moreover, while for ease of reading the application will refer predominantly to synthetic organic reactions as the preferred transformations for which the potential catalysts are screened, those skilled in the art will appreciate that the subject method and libraries may be used to screen for catalysts that exert their influence on other types of transformations, e.g., photochemical energy transfers, inorganic redox reactions, synthetic inorganic reactions, and polymerizations.

As described in greater detail below, there are a wide range of applications for the novel catalysts identified by the subject method. For example, in one embodiment, the subject libraries of catalysts may be generated via the present method with the goal of discovering and optimizing a catalyst for a particular reaction. The selectivity of a potential catalyst can be exploited to transform a single component, e.g. molecule, or stereoisomer, or a subset of the components of a complex mixture. For instance, such selectivity can be utilized in the kinetic resolution of racemic mixtures of enantiomers, or in the enantioselective transformations of meso reactants. Furthermore, if the transformation catalyzed by a catalyst of the subject method is accompanied by a detectable event, e.g. the formation of a precipitate, the evolution of a gas, or the emission of a photon, the combination of the catalyst and the detectable event may form the basis of a test for the presence, in a sample or a complex mixture, of the catalyst's substrate. In a preferred embodiment, a catalyst of the subject method which catalyzed reaction is accompanied by a detectable event forms the basis of a sensor for the presence, and even more preferably for the quantification, of the substrate in a sample. In certain embodiments, the catalysts of the present invention are immobilized and/or isolated within semi-permeable membranes and used as such; catalysts provided in this manner may be reused simply by removal from the reaction mixture of the solid support to which they are attached, or by removal of the semi-permeable membrane in which they are encapsulated, followed by simple rinsing and the like, and immersion in another solution of reactants.

In general, the modular components exploited in the subject method are selected to provide potential catalysts capable of increasing the rate of formation of a product from one or more substrates, e.g. increasing the rate of an intramolecular or intermolecular reaction relative to its rate in the absence of the catalyst. This rate enhancement may involve a role for the catalyst as, for example, a general base or general acid catalyst, an electrostatic catalyst, or a nucleophilic catalyst or other type of covalent catalyst. In one embodiment, catalysts of the present invention catalyze a reaction by lowering the energy of a transition state for the reaction of interest, such as by binding and stabilizing the transition state of the transformation of choice. The selection of the modular components utilized in the subject method will depend upon such factors as their chemical stability, their availability, the level of selectivity sought in the reaction to be catalyzed, the presence of asymmetric centers, the presence of structural elements either know to, or anticipated to, contribute to the creation of a viable catalytic site, and issues of ultimate catalyst solubility.

Strategies for the combination of the modular components to give catalyst libraries are formulated based, in part, on the various factors inferred to have been important in structure-function analyses of established catalysts, including enzymes and non-enzymatic catalysts. For example, in preferred embodiments the library will be derived to include potential catalysts having functional groups capable of interacting, covalently or non-covalently, with a substrate, transition state, and/or a product of a desired reaction. Such functional groups will often include heteroatoms such as nitrogen, oxygen, sulfur, and phosphorus. It will be understood that the modular components may include side-chains or pendant groups capable of interacting with a substrate.

Viable catalysts typically have more than one contact point with a substrate, and the libraries of potential catalysts is synthesized accordingly. For example, the catalysts of the invention are preferably capable of associating with the substrate via at least two contact points, e.g. by hydrogen bonding, electrostatic interactions, hydrophobic interactions, and/or covalent interactions. For catalysts capable of spatial recognition, e.g., discrimination of diastereomers or enantiomers, at least two contact points between the catalyst and the substrate will generally be required.

In preferred embodiments, catalysts are synthesized to provide a predetermined degree of selectivity in the transformation catalyzed. Thus, for example, in certain embodiments, catalysts are capable of kinetic resolution of enantiomers, e.g. catalyzing the reaction of one enantiomer of a substrate in preference to the second enantiomer. High levels of chemo-, regio- and/or stereo-selectivity may be attained by appropriate choice of modular components for construction of a library of catalysts. Thus, catalysts can be synthesized and selected which are highly selective for only a single substrate, or stereoisomer thereof, in a mixture of potential substrates, or stereoisomers thereof.

In preferred embodiments, a given library of potential catalysts includes at least $10^2$, more preferably $10^3$, $10^4$, $10^5$, $10^6$ or even $10^7$ different potential catalysts. The library may, as appropriate, include potential bidentate, tridentate, tetradentate and/or even higher order metal-chelating ligands. Preferably each potential catalyst, subsequent to being freed from the solid support, has a molecular weight less than 7500 amu, more preferably less than 5000, 2500 or even 1000 amu, and even more preferably less than 500 amu.

II. Definitions

For convenience, certain terms employed in the specification and appended claims are collected here.

The terms "Lewis base" and "Lewis basic" are recognized in the art, and refer to a chemical moiety capable of donating a pair of electrons under certain reaction conditions. Examples of Lewis basic moieties include uncharged compounds such as alcohols, thiols, and amines, and charged moieties such as alkoxides, thiolates, carbanions, and a variety of other organic anions.

The terms "Lewis acid" and "Lewis acidic" are art-recognized and refer to chemical moieties which can accept a pair of electrons from a Lewis base as defined above.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma ($\sigma$) constant. This well known constant is described in many references, for instance, J. March, *Advanced Organic Chemistry*, McGraw Hill Book Company, New York, (1977 edition) pp. 251–259. The Hammett constant values are generally negative for electron donating groups ($\sigma[P]=-0.66$ for $NH_2$) and positive for electron withdrawing groups ($\sigma[P]=0.78$ for a nitro group), $\sigma[P]$ indicating para substitution. Exemplary electron-withdrawing groups include nitro, ketone, aldehyde, sulfonyl, trifluoromethyl, —CN, chloride, and the like. Exemplary electron-donating groups include amino, methoxy, and the like.

The term "catalyst" refers to a substance the presence of which increases the rate of a chemical reaction, while not being consumed or undergoing a permanent chemical change itself.

The terms, "bidentate catalyst", "tridentate catalyst", and "tetradentate catalyst" refer to catalysts having, respectively, two, three, and four contact points with the substrate of the catalyst.

The term "complex" as used herein and in the claims means a coordination compound formed by the union of one or more electron-rich and electron-poor molecules or atoms capable of independent existence with one or more electronically poor molecules or atoms, each of which is also capable of independent existence.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably or fewer. Likewise, preferred cycloalkyls have from 3–10 carbon atoms in their ring structure, and more preferably have 5, 6 or 7 carbons in the ring structure.

Moreover, the term "alkyl" (or "lower alkyl") as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an ester, a formyl, or a ketone), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents as described above, for example, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to 12-membered ring structures, more preferably 3- to 7-membered rings, whose ring structures include one to four heteroatoms. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, earbazole, carboline, phenanthridine, acridine, perimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle", as used herein, refers to an aromatic or non-aromatic ring in which each atom of the ring is carbon.

The term "heteroatom" as used herein means an atom of any element other than carbon or hydrogen. Preferred heteroatoms are nitrogen, oxygen, sulfur and phosphorous.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art recognized and refer to both unsubstituted and substituted amines, e.g., a moiety that can be represented by the general formula:

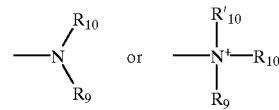

wherein $R_9$, $R_{10}$ and $R'_{10}$ each independently represent a hydrogen, an alkyl, an alkenyl, —$(CH_2)_m$—$R_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In even more preferred embodiments, $R_9$ and $R_{10}$ (and optionally $R'_{10}$) each independently represent a hydrogen, an alkyl, an alkenyl, or —$(CH_2)_m$—$R_8$. Thus, the term "alkylamine" as used herein means an amine group, as defined above, having a substituted or unsubstituted alkyl attached thereto, i.e., at least one of $R_9$ and $R_{10}$ is an alkyl group.

The term "acylamino" is art-recognized and refers to a moiety that can be represented by the general formula:

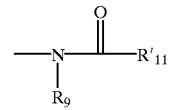

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art recognized as an amino-substituted carbonyl and includes a moiety that can be represented by the general formula:

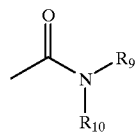

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—(CH$_2$)$_m$—R$_8$, wherein m and R$_8$ are defined above. Representative alkylthio groups include methylthio, ethyl thio, and the like.

The term "carbonyl" is art recognized and includes such moieties as can be represented by the general formula:

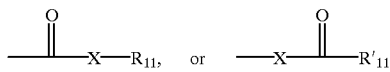

wherein X is a bond or represents an oxygen or a sulfur, and R$_{11}$ represents a hydrogen, an alkyl, an alkenyl, —(CH$_2$)$_m$—R$_8$ or a pharmaceutically acceptable salt, R'$_{11}$ represents a hydrogen, an alkyl, an alkenyl or —(CH$_2$)$_m$—R$_8$, where m and R$_8$ are as defined above. Where X is an oxygen and R$_{11}$ or R'$_{11}$ is not hydrogen, the formula represents an "ester". Where X is an oxygen, and R$_{11}$ is as defined above, the moiety is referred to herein as a carboxyl group, and particularly when R$_{11}$ is a hydrogen, the formula represents a "carboxylic acid". Where X is an oxygen, and R'$_{11}$ is hydrogen, the formula represents a "formyl" group. In general, where the oxygen atom of the above formula is replaced by sulfur, the formula represents a "thiolcarbonyl" group. Where X is a sulfur and R$_{11}$ or R'$_{11}$ is not hydrogen, the formula represents a "thiolester." Where X is a sulfur and R$_{11}$ is hydrogen, the formula represents a "thiolcarboxylic acid." Where X is a sulfur and R$_{11}$' is hydrogen, the formula represents a "thiolformate." On the other hand, where X is a bond, and R$_{11}$ is not hydrogen, the above formula represents a "ketone" group. Where X is a bond, and R$_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—(CH$_2$)$_m$—R$_8$, where m and R$_8$ are described above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled Standard List of Abbreviations. The abbreviations contained in said list, and all abbreviations utilized by organic chemists of ordinary skill in the art are hereby incorporated by reference.

The term "sulfonate" is art recognized and includes a moiety that can be represented by the general formula:

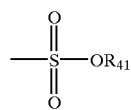

in which R$_{41}$ is an electron pair, hydrogen, alkyl, cycloalkyl, or aryl.

The term "sulfate" is art recognized and includes a moiety that can be represented by the general formula:

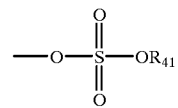

in which R$_{41}$ is as defined above.

The term "sulfonamido" is art recognized and includes a moiety that can be represented by the general formula:

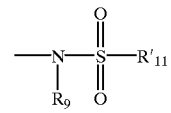

in which R$_9$ and R'$_{11}$, are as defined above.

The term "sulfamoyl" is art-recognized and includes a moiety that can be represented by the general formula:

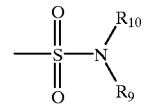

in which R$_9$ and R$_{10}$ are as defined above.

The term "sulfonyl", as used herein, refers to a moiety that can be represented by the general formula:

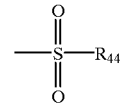

in which R$_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

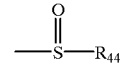

in which R$_{44}$ is selected from the group consisting of hydrogen, alkyl, alkenyl, alkynyl, cycloalkyl, heterocyclyl, aralkyl, or aryl.

A "phosphoryl" can in general be represented by the formula:

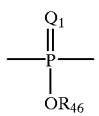

wherein $Q_1$ represented S or O, and $R_{46}$ represents hydrogen, a lower alkyl or an aryl. When used to substitute, e.g., an alkyl, the phosphoryl group of the phosphorylalkyl can be represented by the general formula:

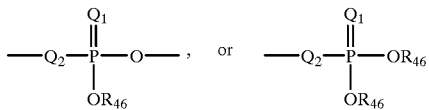

wherein $Q_1$ represented S or O, and each $R_{46}$ independently represents hydrogen, a lower alkyl or an aryl, $Q_2$ represents O, S or N. When $Q_1$ is an S, the phosphoryl moiety is a "phosphorothioate".

A "phosphoramidite" can be represented in the general formula:

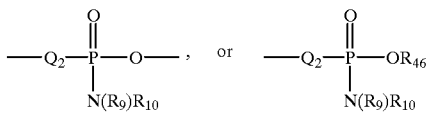

wherein $R_9$ and $R_{10}$ are as defined above, and $Q_2$ represents O, S or N.

A "phosphonamidite" can be represented in the general formula:

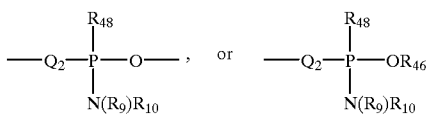

wherein $R_9$ and $R_{10}$ are as defined above, $Q_2$ represents O, S or N, and $R_{48}$ represents a lower alkyl or an aryl, $Q_2$ represents O, S or N.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_7$, m and $R_7$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The phrase "carboxyl-protecting group" as used herein refers to those groups intended to protect a carboxylic acid group, such as the C-terminus of an amino acid or peptide or an acidic or hydroxyl azepine ring substituent, against undesirable reactions during synthetic procedures.

The term "amino-blocking group" is used herein as it is frequently used in synthetic organic chemistry, to refer to a group which will prevent an amino group from participating in a reaction carried out on some other functional group, but which can be removed from the amine when desired.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2$^{nd}$ ed.; Wiley: New York, 1991).

By the terms "amino acid residue" and "peptide residue" is meant an amino acid or peptide molecule without the —OH of its carboxyl group. In general the abbreviations used herein for designating the amino acids and the protective groups are based on recommendations of the IUPAC-IUB Commission on Biochemical Nomenclature (see Biochemistry (1972) 11:1726–1732). For instance Met, Ile, Leu, Ala and Gly represent "residues" of methionine, isoleucine, leucine, alanine and glycine, respectively. By the residue is meant a radical derived from the corresponding α-amino acid by eliminating the OH portion of the carboxyl group and the H portion of the (α-amino group. The term "amino acid side chain" is that part of an amino acid exclusive of the —$CH(NH_2)COOH$ portion, as defined by K. D. Kopple, "Peptides and Amino Acids", W. A. Benjamin Inc., New York and Amsterdam, 1966, pages 2 and 33; examples of such side chains of the common amino acids are —$CH_2CH_2SCH_3$ (the side chain of methionine), —$CH_2$($CH_3$)—$CH_2CH_3$ (the side chain of isoleucine), —$CH_2CH$($CH_3$)$_2$ (the side chain of leucine) or H-(the side chain of glycine).

The term "amino acid" is intended to embrace all compounds, whether natural or synthetic, which include both an amino functionality and an acid functionality, including amino acid analogs and derivatives. Also included in the term "amino acid" are amino acid mimetics such as β-cyanoalanine, norleucine, 3-phosphoserine, homoserine, dihydroxyphenylalanine, 5-hydroxytryptophan, and the like.

In certain embodiments, the amino acids used in the application of this invention are those naturally occurring amino acids found in proteins, or the naturally occurring anabolic or catabolic products of such amino acids which contain amino and carboxyl groups. Particularly suitable amino acid side chains include side chains selected from those of the following amino acids: glycine, alanine, valine, cysteine, leucine, isoleucine, serine, threonine, methionine, glutamic acid, aspartic acid, glutamine, asparagine, lysine, arginine, proline, histidine, phenylalanine, tyrosine, and tryptophan, and those amino acids and amino acid analogs which have been identified as constituents of peptidylglycan bacterial cell walls.

The term "amino acid residue" further includes analogs, derivatives and congeners of any specific amino acid referred to herein, as well as C-terminal or N-terminal protected amino acid derivatives (e.g. modified with an N-terminal or C-terminal protecting group). For example, the present invention contemplates the use of amino acid analogs wherein a side chain is lengthened or shortened while still providing a carboxyl, amino or other reactive precursor functional group for cyclization, as well as amino acid analogs having variant side chains with appropriate functional groups). For instance, the subject compound can include an amino acid analog such as, for example, cyanoalanine, canavanine, djenkolic acid, norleucine, 3-phosphoserine, homoserine, dihydroxy-phenylalanine, 5-hydroxytryptophan, 1-methylhistidine, 3-methylhistidine, diaminopimelic acid, ornithine, or diaminobutyric acid. Other naturally occurring amino acid metabolites or precursors having side chains which are suitable herein will be recognized by those skilled in the art and are included in the scope of the present invention.

Also included are the (D) and (L) stereoisomers of such amino acids when the structure of the amino acid admits of stereoisomeric forms. The configuration of the amino acids and amino acid residues herein are designated by the appropriate symbols (D), (L) or (DL), furthermore when the configuration is not designated the amino acid or residue can have the configuration (D), (L) or (DL). It will be noted that the structure of some of the compounds of this invention includes asymmetric carbon atoms. It is to be understood accordingly that the isomers arising from such asymmetry are included within the scope of this invention. Such isomers can be obtained in substantially pure form by classical separation techniques and by sterically controlled synthesis. For the purposes of this application, unless expressly noted to the contrary, a named amino acid shall be construed to include both the (D) or (L) stereoisomers.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

In the context of this invention, a "saccharide" refers to any monosaccharide or oligosaccharide. A "monosaccharide" is a saccharide that is not hydrolyzable into smaller saccharide units. Monosaccharides include unsubstituted, non-hydrolyzable saccharides such as glucose, as well as modified saccharides in which one or more hydroxyl groups contain substitutions or have been replaced with hydrogen atoms (i.e., deoxy, dideoxy and trideoxy saccharides). Aza-sugars are another example of a modified monosaccharide. Alternatively, a monosaccharide may be present within an oligosaccharide. "Oligosaccharides" are hydrolyzable saccharides that contain two or more monosaccharides linked together in a linear or branched manner. Preferred oligosaccharides for use as turn elements in the subject invention are disaccharide and trisaccharide.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

The term "immobilized", used with respect to a species, refers to a condition in which the species is attached to a surface with an attractive force stronger than attractive forces that are present in the intended environment of use of the surface, and that act on the species. For example, a chelating agent immobilized at a surface, the surface being used to capture a biological molecule from a fluid medium, is attracted to the surface with a force stronger than forces acting on the chelating agent in the fluid medium, for example solvating and turbulent forces.

The term "solid support" refers to a material which is an insoluble matrix, and may (optionally) have a rigid or semi-rigid surface. Such materials will preferably take the form of small beads, pellets, disks, chips, dishes, multi-well plates, wafers or the like, although other forms may be used. In some embodiments, at least one surface of the substrate will be substantially flat. The term "surface" refers to any generally two-dimensional structure on a solid substrate and may have steps, ridges, kinks, terraces, and the like without ceasing to be a surface.

The term "polymeric support", as used herein, refers to a soluble or insoluble polymer to which an amino acid or other chemical moiety can be covalently bonded by reaction with a functional group of the polymeric support. Many suitable polymeric supports are known, and include soluble polymers such as polyethylene glycols or polyvinyl alcohols, as well as insoluble polymers such as polystyrene resins. A suitable polymeric support includes functional groups such as those described below. A polymeric support is termed "soluble" if a polymer, or a polymer-supported compound, is soluble under the conditions employed. However, in general, a soluble polymer can be rendered insoluble under defined conditions. Accordingly, a polymeric support can be soluble under certain conditions and insoluble under other conditions.

The term "functional group of a polymeric support", as used herein, refers to a chemical moiety of a polymeric support that can react with an chemical moiety to form a polymer-supported amino ester. Exemplary functional groups of a polymeric support include hydroxyl and sulthydryl, and the like. Preferred functional groups of a polymeric support will form polymer-supported amino esters that are covalently bound to the polymeric support under mild conditions that do not adversely affect the polymer or the amino ester, and that are sufficiently stable to be isolated.

The term "synthetic" refers to production by in vitro chemical or enzymatic synthesis.

The phrases "individually selective manner" and "individually selective binding", with respect to a recognition event involving a potential catalyst, refers to the recognition event which is specific for, and dependent on, the molecular identity of the potential catalyst.

The term "meso compound" is recognized in the art and means a chemical compound which has at least two chiral centers but is achiral due to an internal plane or point of symmetry.

The term "chiral" refers to molecules which have the property of non-superimposability of the mirror image partner, while the term "achiral" refers to molecules which are superimposable on their mirror image partner. A "prochiral molecule" is a molecule which has the potential to be converted to a chiral molecule in a particular process.

The term "stereoisomers" refers to compounds which have identical chemical constitution, but differ with regard to the arrangement of the atoms or groups in space. In particular, "enantiomers" refer to two stereoisomers of a compound which are non-superimposable mirror images of one another. "Diastereomers", on the other hand, refers to stereoisomers with two or more centers of asymmetry and whose molecules are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product.

The term "regioisomers" refers to compounds which have the same molecular formula but differ in the connectivity of the atoms. Accordingly, a "regioselective process" is one which favors the production of a particular regioisomer over others, e.g., the reaction produces a statistically significant increase in the yield of a certain regioisomer.

The term "epimers" refers to molecules, e.g., saccharides, with identical chemical constitution and containing more than one stereocenter, but which differ in configuration at only one of these stereocenters.

The term "anomers" refers to saccharides that differ in configuration only at the anomeric carbon.

III. Description of Catalyst Libraries.

In general, the invention contemplates the use of modular components, also referred to herein as "subunits", to construct a library of potential catalysts, e.g., that catalyze industrially-relevant organic or inorganic transformations. The modular components are preferably molecular units which can be combined, such as through simultaneous or sequential coupling steps, to construct more complex compounds that are capable of stabilizing the transition state of a given transformation. Such modular components can be associated non-covalently, but are preferably linked covalently to one another, e.g. through amide, ester, thioester, carbamate, carbonate, disulfide, hydrazido, phosphodiester linkages and the like. Conveniently, modular components can be selected to facilitate catalyst assembly, e.g., modular components are selected so that coupling of the individual components may be performed according to efficient, reliable techniques such as amino acid coupling, ester bond formation, and the like.

In one embodiment, illustrated in FIG. 5, the modular components of the subject method include at least two different classes of monomeric chemical moieties. The first group of monomers (or subunits) are referred to herein as "Catalyst Functional Groups" or "CFGs", and include compounds comprising one or more functional groups capable of binding and/or covalently modifying a substrate. The second group of monomers are the "Turn Element Groups" or "TEGs". These units serve as branching points for disposing two or more CFGs in space. In general, the turn elements will be compounds with defined relative and absolute stereochemistry, and are introduced with the notion that such conformational restriction can encourage the formation of a potential binding site in which one or more functionalities of the CFGs interact with a substrate. That is, the turn element arranges the functional groups of the attached CFGs in space with potential conformations that permit the resulting molecule to interact with and catalyze the transformation of the substrate(s).

A third, though optional group of monomeric subunits are the "spacers elements" (not shown in FIG. 5). These compounds are not intended to contain any functional groups which may interact to any great degree with a substrate, rather they are incorporated in the potential catalysts merely to alter the spatial arrangement of functional groups provided by the CFGs. That is, the spacer elements provide greater steric and/or stereochemical diversity in a potential catalyst library.

The libraries can also include "end cap" elements and linkers, which may or may not effect the ability of functional groups of the CFGs to provide a catalytic site. In certain embodiments, the selection of end cap elements can be motivated, at least in part, by such factors as an elements ability to protect CFG substituents, to enhance solubility under certain conditions, and/or to provide certain steric environments around a potential catalytic site formed by CFGs.

In one embodiment, illustrated below in Scheme 1, the library is composed of potential catalysts comprising five elements: 1) a solid support; 2) a first linker domain (Linker$_1$); 3) an amino acid; 4) a second linker domain (Linker$_2$); and 5) a catalytic moiety. The solid support is selected from available supports such that detachment of the potential catalyst from the solid support is possible under mild reaction conditions. Both of the linkers may be selected from the set of difunctional compounds, either with or without sidechains and/or stereocenters, that allow for attachment to the both the solid support and the amino acid, or the amino acid and the catalytic moiety, respectively, via well-characterized linking functional groups.

Scheme 1

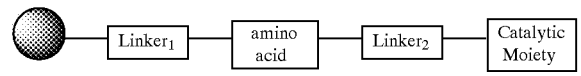

As illustrated by FIG. 5 and Scheme 1, a library of potential catalysts is generated by the combinatorial coupling of one or more linkers and/or turn elements with one or more catalytic moieties (CFGs). Diversity can be generated in the library in any of a number of ways. The potential catalyst library can be generated based upon a variegated population of CFGs. For instance, the CFGs can introduce variation into the library due to the presence in these compounds of different functional groups, as well as differences in the locations (positions of attachment) and dispositions of these functional groups in the CFG structure, e.g., differences arising from chemical and steric features and/or stereochemistry of the CFG. To illustrate, where the CFGs of the potential catalysts of the library include amino acids, the library can be generated with different amino acids, e.g., aspartic acid, glutamic acid, histidine, cysteine, methionine or tyrosine, etc., as well using different isomers of a given amino acid, e.g., L and D isomers.

Heterogeneity in the potential catalyst library can also be introduced by the use of variegated populations of turn elements. As detailed below, the turn elements used in the combinatorial synthesis which constitute the generation of the library can be compounds of different chemical make-up and/or of different stereochemistries. For instance, a library of potential catalysts can be generated from a mixture of different cyclic diols and diamines as turn elements.

The stereochemistry of the turn elements can also be used to variegate the potential catalyst library, such as by the inclusion of different stereoisomers of the same compound, e.g., resulting in diastereomeric, enantiomeric and/or regioisomeric diversity in the library.

Yet another means for introducing diversity into the potential catalyst library is through the use of spacer elements. These elements of the library provide variability in the library with respect to relative distance and/or orientation of the functional groups of the CFGs. For example, a given spacer element may be alkyl chains of varying lengths. It will be understood that the role of an individual spacer element can be effectively duplicated by inclusion of the group in a CFG or turn element.

The number of diversomers at any given position in the potential catalyst library is the sum of different chemical moieties and/or stereoisomers which can occur at that position. Thus, in an illustrative embodiment where the potential catalysts of a given library have one turn element position, the members of the library can be represented by the general formula $T(-R)_n$ where T represents a turn element, n is the number of substituted branch points on the turn element (e.g., an integer greater than or equal to 2) and R represents, independently for each of its n occurrences, a sidechain comprising one or more CFGs. The number of different potential catalysts which can be provided in such a library is given by the formula $TE \times [Z_1 \times Z_2 \times \ldots Z_m]_1 \times [Z_1 \times Z_2 \times \ldots Z_m]_2 \times \ldots [Z_1 \times Z_2 \times \ldots Z_m]_n$, where TE is the number of turn element groups, and each Z is the number of CFGs (or other diversomer) at each of m combinatorial positions in each of the n ligand sidechains branching from the turn element. The number of diversomers at any given position in the library, be it a turn element or in a moiety provided in a sidechain of interest, is the sum of different chemical moieties and/or stereoisomers which can occur at that position. In preferred embodiments, the potential catalyst library includes at least 100 different molecular species, more preferably at least $10^3$, $10^4$ or $10^5$ different species of potential catalyst, though libraries within the range of conventional combinatorial synthesis techniques are anticipated, e.g., exceeding $10^3$ distinct members.

a). Catalyst Functional Groups

The role of the CFG moieties is to provide functional moieties in the catalyst structure that can bind to and/or covalently modify a substrate or substrates. As set out above, such groups can provide in a catalyst the ability to selectively bind a substrate, stabilize a transition state, and/or participate as a covalent catalyst. That is, the combinatorial synthesis of catalyst libraries from CFG monomers is intended to provide poly-functionalized compounds. In general, the catalysts of the present invention will include organic electron donor or acceptor moieties. Accordingly, in a preferred embodiment, the subject libraries are generated with CFGs including one or more functional groups having an electron pair donor (Lewis base) which can act as a nucleophile, and/or an electron pair acceptor (Lewis acid) which can acts as an electrophile, as appropriate, for the reaction to be catalyzed. In the case of the former, the functional group will preferably be a strongly acidic group, e.g., with a pKa less than about 7, and more preferably less than 5, which can produce a conjugate base that, under the reaction conditions, is a strong enough Lewis base to donate an electron pair. In the case of the latter, the functional group will preferably be a hydrogen-bond donor, an atom with a vacant orbital, or an atom capable exchanging one bound Lewis base for another.

As set out above, the term "Lewis base" refers to any chemical species which is an electron pair donor. The types of Lewis basic functional groups useful in the subject catalysts are too numerous to categorize, though in preferred embodiments such compounds will include bases which bear atoms from Periodic Groups 15 and 16.

Lewis bases from Group 15 contain nitrogen, phosphorous, arsenic, antimony or bismuth atoms as electron pair donors. Preferable Lewis bases from Group 15 contain nitrogen, phosphorous, and antimony, and more preferably, nitrogen or phosphorous.

Lewis bases from Group 16 contain oxygen, sulfur, or selenium atoms as electron pair donors. Preferable Lewis bases from Group 16 contain oxygen or sulfur.

Exemplary Lewis basic moieties which can be used in the CFGs include amines (primary, secondary, and tertiary) and aromatic amines, amino groups, amido groups, nitro groups, nitroso groups, amino alcohols, nitriles, imino groups, isonitriles, cyanates, isocynates, phosphates, phosphonates, phosphites, (substituted) phosphines, phosphine oxides, phosphorothioates, phosphoramidates, phosphonamidites, hydroxyls, carbonyls (e.g., carboxyl, ester and formyl groups), aldehydes, ketones, ethers, carbamoyl groups, thiols, sulfides, thiocarbonyls (e.g., thiolcarboxyl, thiolester and thiolformyl groups), thioethers, mercaptans, sulfonic acids, sulfoxides, sulfates, sulfonates, sulfones, sulfonamides, sulfamoyls and sulfinyls.

Illustrative of suitable CFGs are those organic compounds containing at least one Lewis basic nitrogen, sulfur, phosphorous or oxygen atom or a combination of such nitrogen, sulfur, phosphorous and oxygen atoms. The carbon atoms of the CFGs can be part of an aliphatic, cycloaliphatic or aromatic moiety. Typically, the CFG will contain at least 2 carbon atoms, though generally no more than 40 carbon atoms. In addition to the organic Lewis base(s), the CFG may also contain other atoms and/or groups as substituents, such as alkyl, aryl and halogen substituents. Catalytic moieties useful in generating potential catalysts in the subject method include linear and branched functional olefinic compounds having at least one functional terminal reactive group which can act as a Lewis base. Examples of the Lewis base are: amines, particularly alkylamines and arylamines, including methylamine, diphenylamine, trimethylamine, triethylamine, N,N-dimethylaniline, methyldiphenylaniline, pyridine, aniline, morpholine, N-methylmorpholine, pyrrolidine, N-methylpyrrolidine, piperidine, N-methylpiperidine, cyclohexylamine, n-butylamine, dimethyloxazoline, imidazole, N-methylimidazole, N,N-dimethylethanolamine, N,N-diethylethanolimine, N,N-dipropylethanolamine, N,N-dibutylethanolamine, N,N-dimethylisopropanolamine, N,N-diethylisopropanolamine, N,N-dipropylisopropanolamine, N,N-dibutylisopropanolamine, N-methyldiethanolamine, N-ethyldiethanolamine, N-propyldiethanolamine, N-butyldiethanolamine, N-methyldiisopropanolamine, N-ethyldiisopropanolamine, N-propyldiisopropanolamine, N-butyldiisopropanolamine, triethylamine, triisopropanolamine, tri-s-butanolamine and the like; amides, such as N,N-dimethylformamide, N,N-dimethylacetamide, N-methylpyrrolidone, hexamethylphosphoric acid triamide and the like; sulfoxide compounds, such as dimethylsulfoxide and the like; ethers such as dimethyl ether, diethyl ether, tetrahydrofuran, dioxane and the like; thioethers such as dimethylsulfide, diethyl thioether, tetrahydrothiophene and the like; esters of phosphoric acid, such as trimethyl phosphate, triethylphosphate, tributyl phosphate and the like; esters of boric acid, such as trimethyl borate and the like; esters of carboxylic acids, such as ethyl acetate, butyl acetate, ethyl benzoate and the like; esters of carbonic acid, such as ethylene carbonate and the like; phosphines, including di- and trialkylphosphines, such as tributylphosphine, triethylphosphine, triphenylphosphine, diphenylphosphine and the like; and monohydroxylic and polyhydroxylicalcohols of from 1 to 30 carbon atoms such as methyl alcohol, ethyl alcohol, n-propyl alcohol, isopropyl alcohol, n-butyl alcohol, isobutyl alcohol, tert-butyl alcohol, n-pentyl alcohol, isopentyl alcohol, 2-methyl-1-butyl alcohol, 2-methyl-2-butyl alcohol, n-hexyl alcohol, n-heptyl alcohol, n-octyl alcohol, isooctyl alcohol, 2-ethylhexyl alcohol, n-nonyl alcohol, n-decyl alcohol, 1,5-pentanediol, 1,6-hexanediol, allyl alcohol, crotyl alcohol, 3-hexene-1-ol, citronellol, cyclopentanol, cyclohexanol, salicyl alcohol, benzyl alcohol, phenethyl alcohol, cinnamyl alcohol, and the like.

As a further illustration, exemplary CFGs include bifunctional compounds such as amino acids, hydroxy acids, hydroxy thiols, mercapto amines, and the like. The term "amino acid" is intended to embrace all compounds, whether natural or synthetic, which include both an amino functionality and an acid functionality, including amino acid analogs and derivatives. Also included in the term "amino acid" are amino acid mimetics such as β-cyanoalanine, norleucine, 3-phosphoserine, homoserine, dihydroxyphenylalanine, 5-hydroxytryptophan, and the like. Such CFGs can include any and/or all stereoisomers when the modular component admits of such isomers.

Other exemplary modular components include nucleic acids and nucleic acid analogs and derivatives, diacids, diamines, and the like. In certain embodiments, modular components of different types can be combined to form a library of potential catalysts. For example, a diacid modular component can react with a diamine modular component to produce an amide bond.

In certain preferred embodiments, if a variegated potential catalyst library comprises amino acids, at least one modular component will be a non-naturally-occurring amino acid. The process of selecting suitable non-natural amino acids for use in the present invention will parallel the selection of natural amino acids in the invention. For example, preferred embodiments of the natural amino acids identified above include nitrogen or sulfur atoms, e.g., histidine and cysteine. Similarly, preferred non-natural amino acids will also incorporate a nitrogen and/or a sulfur center.

If desired, one functionality can be selectively protected or blocked to permit reaction of an unblocked functional group. Thus, for example, amino acids, nucleotides, and saccharides can be blocked and deblocked according to known procedures.

b). Turn Elements

A salient feature of the turn elements of the subject catalysts is that they can provide spatial preorganization of the CFGs into conformations which can be complementary to the geometries of a substrate or substrates, a transition state, intermediate, and/or a product of a desired reaction. The combinatorial approach allows the optimization of catalytic rate enhancements and/or specificities by accessing large numbers of spatial arrangements of CFGs.

In addition to availability, reactivity and stability, a criteria in the selection of turn elements for generating the potential catalyst library is the "rigidity" of the molecule. For purposes of the invention described herein, the term "rigid" refers to the physical state of molecular structures having fewer intramolecular rotational degrees of freedom than a simple linear chain. The choice of turn elements preferably favors groups with limited degrees of freedoms, though examples of linear elements are provided below as well. In preferred embodiments, an individual turn element has a reduced number of internally rotatable bonds, e.g., relative to a straight chain alkyl.

The stereochemical constraints of a cyclic element can serve to orient and predispose the CFGs of its substituents and thereby impart maximal interaction with the, e.g. transition state of a transformation. In this manner, a turn element can be selected with optimized complementarity and pre-organization in mind, e.g., for reducing the entropic cost of recognition of the transition state.

The ability to utilize stereochemical diversity in the turn element(s) further illustrates this point. Beginning with a meso-epoxide, enantioselective ring opening can provide enantiomerically enriched turn elements which can be further derivatized with, e.g., stereochemically defined CFGs to yield libraries of diastereomerically variegated compounds.

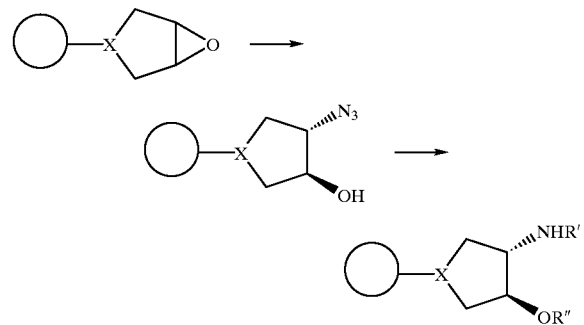

To further elaborate, in one representative embodiment, Tentagel, a polystyrene-polyethylene glycol copolymer resin (Rappe Polymere, Tubingen, Germany) having a cleavable linking arm is cleaved by strong acidic conditions (such as trifluoroacetic acid), is esterified with 4-nitrophenyl chloroformate. The resin is then reacted with tetrahydro-1aH-cyclopenta[b]oxiren-3-ylmethanol to yield the epoxide-derived resin.

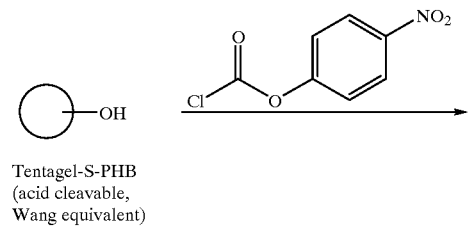

Tentagel-S-PHB
(acid cleavable,
Wang equivalent)

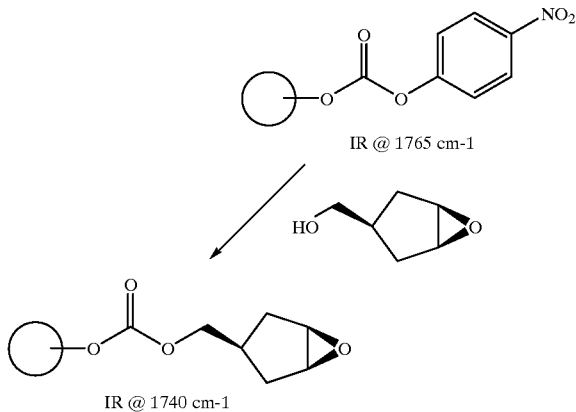

IR @ 1765 cm-1

IR @ 1740 cm-1

The epoxide is then enantioselectively opened with trimethylsilyl azide (TMSN₃) in the presence of a chiral salen catalyst [1,2,-bis(3,5-di-tert-butylsalicylide-amino)cyclohexane:Cr, e.g., see U.S. Pat. No. 5,665,890] to yield, in the illustrate reaction, the enantiomerically enriched 3-azido-4-trimethylsilyloxy-cyclopentyl derived polymer. This serves as a useful

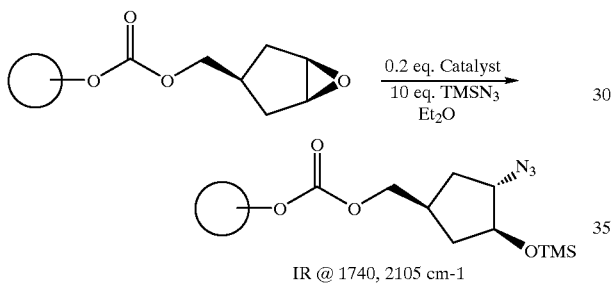

IR @ 1740, 2105 cm-1 intermediate in the generation of the subject libraries, and the technique can be generally applied to many other epoxides.

In preferred embodiments, the turn element is a ring moiety, e.g., a carbocyclic or heterocyclic moiety which may be monocyclic or polycyclic, aromatic or non-aromatic. Exemplary turn elements of this type include, but are not limited to, acridarsine, acridine, anthracene, arsindole, arsinoline, azepane, benzene, carbazole, carboline, chromene, cinnoline, furan, furazan, hexahydropyridazine, hexahydropyrimidine, imidazole, indane, indazole, indole, indolizine, isoarsindole, isobenzofuran, isochromene, isoindole, isophosphindole, isophosphinoline, isoquinoline, isorasinoline, isothiazole, isoxazole, morpholine, naphthalene, naphthyridine, oxazole, oxolane, perimidine, phenanthrene, phenanthridine, phenanthroline, phenarsazine, phenazine, phenomercurazine, phenomercurin, phenophosphazine, phenoselenazine, phenotellurazine, phenothiarsine, phenoxantimonin, phenoxaphosphine, phenoxarsine, phenoxaselenin, phenoxatellurin, phenothiazine, phenoxathiin, phenoxazine, phosphanthene, phosphindole, phosphinoline, phthalazine, piperazine, piperidine, pteridine, purine, pyran, pyrazine, pyrazole, pyridazine, pyridine, pyrimidine, pyrrolidine, pyrrolizine, quinazoline, quinoline, quinolizine, quinoxaline (such as pyrrole), selenanthrene, selenophene, tellurophene, tetrahydrofuran, tetrahydrothiophene, thianthrene, thiazole, thiolane, thiophene or xanthene.

Thus, in one embodiment the potential catalysts of the library can be represented by the general formula:

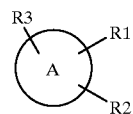

wherein

A represents a carbocycle or heterocycle which can be monocyclic or polycyclic, aromatic or non-aromatic;

$R^1$ and $R_2$ each represent, independently for each occurrence in a potential catalyst of a library, an CFG including a moiety selected from the group consisting of amines (primary, secondary, and tertiary and aromatic amines), amino groups, amido groups, nitro groups, nitroso groups, amino alcohols, nitriles, imino groups, phosphates, phosphonates, phosphites, (substituted) phosphines, phosphine oxides, phosphorothioates, phosphoramidates, phosphonamidites, hydroxyls, carbonyls (e.g., carboxyl, ester and formyl groups), aldehydes, ketones, ethers, carbamoyl groups, thiols, sulfides, thiocarbonyls (e.g., thiolcarboxyl, thiolester and thiolformyl groups), thioethers, mercaptans, sulfonic acids, sulfates, sulfonates, sulfonones, sulfonamides, sulfamoyls and sulfinyls, or alkyl, alkenyl or alkynyl groups (preferably in the range of $C_1$–$C_{30}$) substituted therewith; and $R_3$ is absent or represents one or more further CFG substitutions to the ring A, each occurrence of which independently includes a moiety selected from the group consisting of amines (primary, secondary, and tertiary and aromatic amines), amino groups, amido groups, nitro groups, nitroso groups, amino alcohols, nitriles, imino groups, phosphates, phosphonates, phosphites, (substituted) phosphines, phosphine oxides, phosphorothioates, phosphoramidates, phosphonamidites, hydroxyls, carbonyls (e.g., carboxyl, ester and formyl groups), aldehydes, ketones, ethers, carbamoyl groups, thiols, sulfides, thiocarbonyls (e.g., thiolcarboxyl, thiolester and thiolformyl groups), thioethers, mercaptans, sulfonic acids, sulfates, sulfonates, sulfonones, sulfonamides, sulfamoyls and sulfinyls, or alkyl, alkenyl, alkynyl or aryl groups (preferably in the range of $C_1$–$C_{30}$) substituted therewith.

Another source of elements for the subject method are the conformationally constrained mimetics used to generate peptidomimetics, for example, the benzodiazepines (see, e.g., James et al. (1993) Science 260:1937), substituted lactam rings (Garvey et al. in Peptides: Chemistry and Biology, G. R. Marshall ed., ESCOM Publisher: Leiden, Netherlands, 1988, p123) and phenoxathin ring systems (Kemp et al. (1988) Tetrahedron Lett. 29:4931; Kemp et al. (1988) Tetrahedron Lett. 29:4935). Thus, many of the conformational motifs used in the peptidomimetic art, such as β-turns, are used to advantage in the present potential catalyst design protocol.

To illustrate, an element of the subject method can be either an external or internal β-turn mimetic. External β-turn mimetics were the first to be produced. Friedinger et al. (1980) Science 210:656–658, discloses a conformationally constrained nonpeptide β-turn mimetic monocyclic lactam. In preferred embodiments, the element is a substituted lactam, e.g., either a monocyclic or a polycyclic lactam. As used herein, a "lactam" includes any organic ring having an amide linkage internal to the ring, as for example β-carbolines containing a γ- or δ-lactam ring.

In still another embodiment, an element of the potential catalysts may be a polycyclic moiety, e.g., having two or more rings with two or more common (bridgehead) ring atoms, e.g., so that there are three or more different paths (bridging substituents) between the bridgehead atoms.

In certain instances, an element of the potential catalysts will be a polycyclic alkane, or bridged carbocycle, and may preferably be a bicyclic alkane. The generic name for bicyclic alkanes is bicyclo[x.y.z]alkane, where x, y and z are the numbers of intervening carbon atoms on the three paths between the two bridgehead carbons. Similar nomenclature is used for bridged heterocycles. Exemplary bicyclic alkanes for use in the present invention include such compounds as: 2-methylbicyclo[2.1.0]pentane, bicyclo[2.1.1]hexane, 1,4-dimethylbicyclo[2.2.0]hexane, bicyclo[2.2.1]heptane (norbornane), 7,7-dimethylbicyclo[2.2.1]heptane, endo-2-isopropyl-7,7-dimethylbicyclo[2.2.1]heptane, trans-bicyclo[4.4.0]decan-3-one, bicyclo[2.2.2]octane, 1,4-diisopropylbicyclo[2.2.2]octane, (2S,3S)-2-ethyl-3-methyl-bicyclo[2.2.2]octane, bicyclo[3.1.0]hexane, 2,6,6-trimethylbicyclo[3.1.1]heptane, bicyclo-[3.2.0]heptane, bicyclo[3.2.2]nonane, bicyclo[3.3.0]octane, 1,2-dimethylbicyclo-[3.3.0]octane, bicyclo[3.3.3]undecane, bicyclo[4.1.0]heptane, (1S,2R,4S,6R)-4-ethyl-2-isopropylbicyclo[4.1.0]heptane, cis-bicyclo[4.2.1]nonane, 1,9-dimethylbicyclo[4.2.1]nonane, trans-1,6-dibromobicyclo[4.3.0]nonane, 1-methyl-8-propylbicyclo-[4.3.0]nonane, bicyclo[4.3.2]undecane, cis-bicyclo[4.4.0]decane (cis-decalin), trans-bicyclo[4.4.0]decane (trans-decalin), and trans-bicyclo[4.4.0]decan-3-one, In other instances, the polycycle used can be a bridged heterocycle. The bridging substituent can be, for example, an azimino (—N=N—HN—), an azo (—N=N—), a biimino (—NH—NH—), an epidioxy (—O—O—), an epidithio (—S—S—), an epithio (—S1—), an epithioxi-mino (—S—O—NH—), an epoxy (—O—), an epoxyimino (—O—NH—), an epoxynitrilo (—O—N=), an epoxythio (—O—S—), an epoxythioxy (—O—S—O—), a furano (—C$_4$H$_2$O—), an imino (—NH—), or a nitrilo (—N=) moiety. Exemplary bridged heterocycles include 7-azabicyclo-[2.2.1]heptane, and 3,6,8-trioxabicyclo[3.2.2]nonane, 2,6-dioxabicyclo[3.2.1]oct-7-yl, and substituted forms thereof.

Preferred bicyclic moieties are those in which each bridging substituent includes at least one atom between each bridging atom, e.g., x, y and z are each integers equal to or greater than 1.

In similar fashion, other cyclic elements include polycycles having three or more bridging atoms and three or more rings, e.g., such as the so-called polycyclic cage compounds. For instance, the turn element can be derived from adamantine, diamantane, cubane, quadricyclene (tetracyclo[2.2.1.0$^{(2,6)}$.0$^{(3,5)}$]heptane), to name but a few. Compounds containing adamantane subunits, for example, have been of interest to chemists due to the rigid structure and well-defined substitution chemistry of the tricyclic compound. This feature of the adamantane molecule can be exploited to generate the subject potential catalysts. Moreover, numerous synthetic schemes have been derived for substituting the adamantane rings. See, for example, U.S. Pat. Nos. 3,388,164 and 3,391,142 (synthesis of aminoadamantane); Molle et al. (1982) *J Org Chem* 47:4120 (carbocation chemistry of the adamantane system), and U.S. Pat. No. 5,599,998 (substitution of halo-adamantanes).

In another embodiment, an element of the potential catalysts is a saccharide, preferably a mono-, di- or trisaccharide. In preferred embodiments, the element is derived from a pentose or hexose sugar or azasugar. Where the saccharide is attached to the solid support, it can be attached glycosidically, retaining the anomeric carbon of the sugar. In other embodiments, the saccharides can be subjected to reductive amination in the presence of a solid support bearing a terminal amine functionality, thereby converting the reducing sugar to an aminoalditol. In an illustrative embodiment of the latter, a pentose sugar having a particular stereoconfiguration about each chiral center is coupled to amino groups of polymer (such as amino ethylated polyacrylamide). For instance, the reducing end of the sugar can be attached to an amino-functionalized surface by reductive amination in the presence of sodium cyanoborohydride.

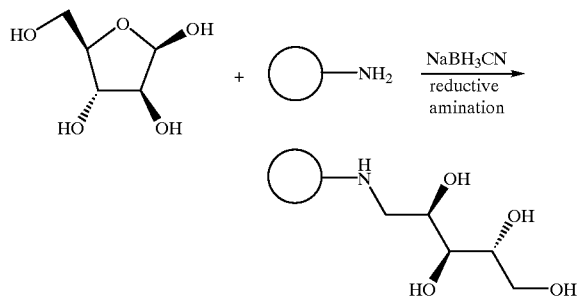

The resulting 1,2,3,4-pentanetetraol provides hydroxyl groups at several asymmetric carbons which are available for further derivatization. Because a myriad of cheap, enatiomerically-pure sugars are readily available, such sugars represent an excellent source for a chiral pool of library elements, e.g., which introduce stereochemical diversity. Specific examples of monosaccharides useful in the subject invention include hexoses such as glucose, mannose, galactose, glucosamine, mannosamine and galactosamine; and pentoses such as arabinose, xylose and ribose. Specific examples of oligosaccharides, on the other hand, include disaccharides such as maltose, lactose, trehalose, cellobiose, isomaltose, gentiobiose, melibiose, laminaribiose, chitobiose, xylobiose, mannobiose and sophorose.

In yet another embodiment, an element of the libraries is an azasugar or a phosphanyl sugar, or a derivative thereof. Azasugars include a class of saccharides in which the ring oxygen is replaced by a nitrogen, or in which a ring carbon is replaced with an amino group. A six-membered ring azasugar can be referred to as an azapyranose or a polyhydroxylated piperidine compound. A five-membered ring azasugar can be referred to as an azafuranose or a polyhydroxylated pyrrolidine. An azasugar can also be named as an aza derivative of an otherwise systematically or trivially named pyranose or furanose monosaccharide. Exemplary azasugars which can be used as turn elements may be derived from piperidines (azapyranoses) or from pyrrolidines (azafuranoses). Likewise, phosphanyl sugars include sugars in which a ring postion is replaced with a phosphanyl group.

An exemplary use of an azasugar element is illustrated below. An azapyranose, such as the (2S,3S,4S,5R)-azapyranose shown, can be coupled by well-known protocols to an amine-containing support using a homobifunctional element such as malonic acid (n=1), succinic acid (n=2) or the like as a tether to the support.

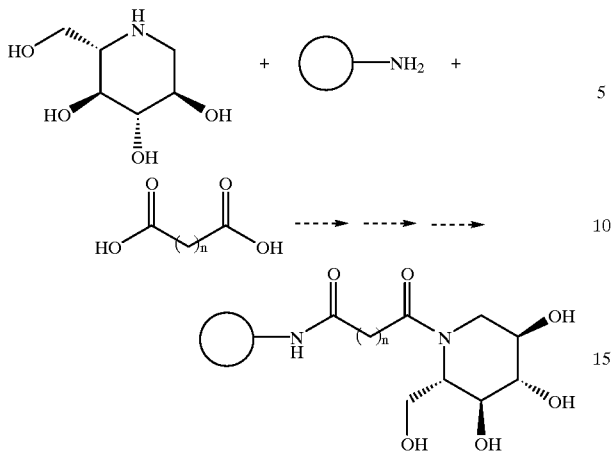
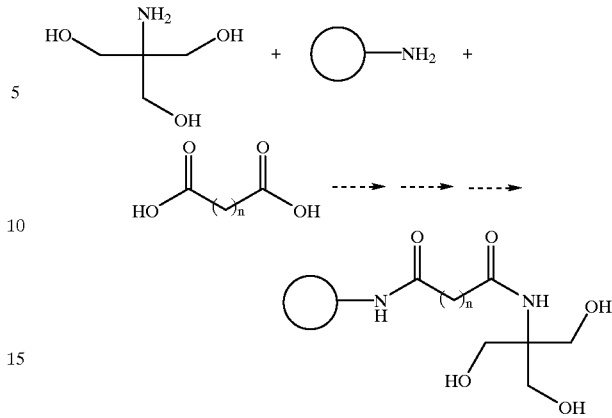

Naturally occurring azasugars can be used as elements. Exemplary azasugars of this type include 1-deoxynojirimycin (1,5-dideoxy-1,5-imino-D-glucitol), 1-deoxymannojirimycin (1,5-dideoxy-1,5-imino-D-mannitol), and castanospermine (1,6,7,8-tetrahydroxy-octahydroindolizine). 1-Deoxynojirimycin is isolated from plants of the genus Morus (Yagi et al., *Nippon Nogei Kagaku Kaishi* 1976, 50:5751; Vasella et al., *Helv. Chim. Acta*, 1982 65:1134) and from strains of Bacillus (Daigo et al., *Chem. Pharm. Bull.* 1986, 34:2243). 1-Deoxymannojirimycin is isolated from the legume Lonchocarpus (Fellows et al., *J. C. S. Chem. Comm.* 1979, 977). Castanospermine is a plant alkaloid isolated from seeds of an Australian chestnut tree, *Castanospermum australe* (Saul et al. *Arch. Biochem. Biophys.* 1983, 221:593].

Both synthetic and semi-synthetic routes have also been used in the syntheses of azasugars and can be readily adapted for generating elements in the subject libraries. For instance, synthetic routes to azasugars have commonly entailed processes such as azide displacement/reduction and N-alkylative cyclization with extensive protecting-group manipulation. See, for example, Paulsen et al. (1967) *Chem. Ber.* 100:802; Inouye et al. (1968) *Tetrahedron* 23:2125; Saeki et al. (1968) *Chem. Pharm. Bull.* 11:2477; Kinast et al. (1981) *Angew. Chem. Int. Ed. Engl.* 20:805; U.S. Pat. No. 4,266,025; Vasella et al. (1982) *Helv. Chim. Acta* 65:1134; U.S. Pat. No. 4,611,058; Bernotas et al. (1985) *Tetrahedron Lett.* 26:1123; Setoi et al. (1986) *Chem. Pharm. Bull.* 34:2642; Broxterman et al. (1987) *Rec. Trav. Chim. Pays-Bas* 106:571; Fleet et al. (1987) *Tetrahedron* 43:979; Iida et al. (1987) *J. Org. Chem.* 52:3337; Ziegler et al. (1988) *Angew Chem. Int. Ed. Engl.* 27:716; Schmidt et al. (1989) *Liebigs Ann. Chem.* 423; Chida et al. (1989) *J. Chem. Soc., Chem. Commun.* 1230; Beaupere et al. (1989) *Carbohydr. Res.* 191:163; von der Osten et al. (1989) *J. Am. Chem. Soc.* 111:3924; Ikota, N. (1989) *Heterocycles* 22:1469; Tsuda et al. (1989) *Chem. Pharm Bull* 37:2673; Fleet et al. (1990) *Tetrahedron Lett.* 31:490; Anzeveno et al. (1990) *Tetrahedron Lett.* 31:2085; and Dax et al. (1990) *Carbohydr. Chem.* 9:479.

Natural sugars have been used as starting materials for the production of azasugars, though multiple protection and deprotection steps are required. For example, glucose can be used in the synthesis of 1-deoxynojirimycin and 1-deoxymannojirimycin (Bernotas et al., 1985, supra; and Chen et al., (1990) *Tetrahedron Lett.* 31:2229).

TRIS and related compounds can also be ideal bi-functional molecules for use in the subject libraries. To illustrate:

c. End Caps

Another potential component in the synthesis of the subject catalyst libraries are so-called "end cap" units. In general, these components can serve several different purposes.

They can, for example, be used as protecting groups for the ends of each string of CFG subunits substituted on a turn element. However, the end caps can also play a role in the catalytic activity of a potential catalyst, e.g. contributing to both affinity and specificity. For instance, the end cap groups can themselves include Lewis acidic and/or basic moieties which contribute to catalytic activity, and in this regard they may also be considered CFG groups. The selection of the end cap can also provide steric diversity in a library. Likewise, by the use of electron-withdrawing and/or electron-donating groups on the end cap, the Lewis basicity of neighboring CFG units may be influenced. The selection of the end cap can also be used to affect solubility of the potential catalyst.

Examples of end cap groups for carboxyl groups include, for example, benzyl ester, cyclohexyl ester, 4-nitrobenzyl ester, t-butyl ester, 4-pyridylmethyl ester, and the like.

Examples of suitable end cap groups for amine include acyl protecting groups such as, to illustrate, formyl, dansyl, acetyl, benzoyl, trifluoroacetyl, succinyl, methoxysuccinyl, benzyl and substituted benzyl such as 3,4-dimethoxybenzyl, o-nitrobenzyl, and triphenylmethyl; those of the formula —COOR where R includes such groups as methyl, ethyl, propyl, isopropyl, 2,2,2-trichloroethyl, 1-methyl-1-phenylethyl, isobutyl, t-butyl, t-amyl, vinyl, allyl, phenyl, benzyl, p-nitrobenzyl, o-nitrobenzyl, and 2,4-dichlorobenzyl; acyl groups and substituted acyl such as formyl, acetyl, chloroacetyl, dichloroacetyl, trichloroacetyl, trifluoroacetyl, benzoyl, and p-methoxybenzoyl; and other groups such as methanesulfonyl, p-toluenesulfonyl, p-bromobenzenesulfonyl, p-nitrophenylethyl, and p-toluenesulfonyl-aminocarbonyl. Preferred amino-blocking groups are benzyl (—CH$_2$C$_6$H$_5$), acyl [C(O)R] or SiR$_3$ where R is C$_1$–C$_4$ alkyl, halomethyl, or 2-halo-substituted-(C$_2$–C$_4$ alkoxy), aromatic urethane protecting groups as, for example, carbonylbenzyloxy (Cbz); and aliphatic urethane protecting groups such as t-butyloxycarbonyl (Boc) or 9-fluorenylmethoxycarbonyl (FMOC).

A set of preferred reagents for installing end cap units on amines include: ethanoyl chloride (Acy); 2,2-dimethylpropanoyl chloride (Piv); naphthalenecarbonyl chloride (Nap); 1,3-benzodioxole-5-carbonyl chloride (Pip);

methyl 2-chlorocarbonylacetate (Mal); pipicolic or 2-pyridinecarboxylic acid (Pic); 5-oxo-2-pyrrolidinecarboxylic acid (Pga); 4-methyl-1-benzenesulfonyl chloride (Tos); and phenylmethanamide (ICN).

To incorporate amino- and/or carboxyl-protecting groups, conventional solid phase peptide synthesis methods and other conventional techniques can also be adapted to the subject method. Incorporation of amino-blocking group, for example, can be achieved while the synthesized compound is still attached to the resin, for instance by treatment with a suitable anhydride. To incorporate an acetyl protecting group, for instance, the resincoupled coupled can be treated with 20% acetic anhydride.

IV. Detection of Catalytic Activity

Libraries of potential catalysts can be screened for catalytic activity according to a variety of techniques, some of which are known in the art. If a transformation catalyzed by a catalyst of the subject method is accompanied by a detectable event, e.g. the formation of a precipitate, the evolution of a gas, or the emission of a photon, the combination of the catalyst and the detectable event may form the basis of a test for the presence, in a sample or a complex mixture, of the catalyst's substrate. Conversely, exposure of a library of potential catalysts to a known substrate for a desired type of catalytic activity, wherein the substrate during or upon transformation by a catalyst generates a detectable event, may form the basis of a screening method for that type of catalytic activity.

Libraries of potential catalysts can also be screened with reagents which detect functional properties of a catalyst or catalysts. For example, a probe moiety can be combined with a label moiety, such as a dye, a fluorophore, a radiolabel, or the like, to detect the presence of a target (e.g., by staining a bead). The probe can bind reversibly or irreversibly to the target. For example, a library of potential catalysts may be screened for the presence of Lewis-acidic moieties by contacting the library with a compound, e.g., a compound comprising a Lewis basic functional group, which interacts reversibly with such Lewis acids, and in which the compound comprises additionally a label moiety. Any potential catalyst which comprises a Lewis-acidic moiety will then become associated, through the Lewis basic moiety, with a label, which in turn can be detected.

The subject methods may be utilized to discover and optimize catalysts for a wide range of chemical transformations. Catalysts may be discovered and optimized for transformations selected from the set comprising kinetic resolutions, regioselective reactions, chemoselective reactions, diastereoselective reactions, stereoselective reactions, functional group interconversions, hydrogenations, oxidations, reductions, resolutions of racemic mixtures, cycloadditions, sigmatropic rearrangements, electrocyclic reactions, ring-openings, carbonyl additions, carbonyl reductions, olefin additions, olefin reductions, imine additions, imine reductions, olefin epoxidations, olefin aziridinations, carbon-carbon bond formations, carbon-heteroatom bond formations, and heteroatom-heteroatom bond formations.

V. Tagging/Deconvolution techniques for libraries

A) Direct Characterization

A growing trend in the field of combinatorial chemistry is to exploit the sensitivity of techniques such as mass spectrometry (MS), e.g., which can be used to characterize sub-femtomolar amounts of compound, and to directly determine the chemical constitution of a compound selected from a combinatorial library. For instance, where the library is provided on an insoluble support matrix, discrete populations of compounds can be first released from the support and characterized by MS. In other embodiments, as part of the MS sample preparation technique, such MS techniques as MALDI can be used to release a compound from the matrix, particularly where a labile bond is used originally to tether the compound to the matrix. For instance, a bead selected from the a potential catalyst library can be irradiated in a MALDI step in order to release the potential catalyst from the matrix and ionize the potential catalyst for MS analysis.

B) Multipin Synthesis

One form that the potential catalyst library of the subject method can take is the multipin library format. Briefly, Geysen and co-workers (Geysen et al. (1984) *PNAS* 81:3998–4002) introduced a method for generating compound libraries by a parallel synthesis on polyacrylic acid-grated polyethylene pins arrayed in the microtitre plate format. The Geysen technique can be used to synthesize and screen thousands of potential catalysts per week using the multipin method, and the tethered potential catalysts may be reused in many assays. Appropriate linker moieties can also been appended to the pins so that the potential catalysts may be cleaved from the supports after synthesis for assessment of purity and further evaluation (cf, Bray et al. (1990) *Tetrahedron Lett* 31:5811–5814; Valerio et al. (1991) *Anal Biochem* 197:168–177; Bray et al. (1991) *Tetrahedron Lett* 32:6163–6166).

C) Divide-Couple-Recombine

In yet another embodiment, a variegated library of potential catalysts can be provided on a set of beads utilizing the strategy of divide-couple-recombine (see, e.g., Houghten (1985) *PNAS* 82:5131–5135; and U.S. Pat. Nos. 4,631,211; 5,440,016; 5,480,971). Briefly, as the name implies, at each synthesis step where degeneracy is introduced into the library, the beads are divided into separate groups equal to the number of different substituents to be added at a particular position in the potential catalyst library, the different substituents coupled in separate reactions, and the beads recombined into one pool for the next iteration.

In one embodiment, the divide-couple-recombine strategy can be carried out using an analogous approach to the so-called "tea bag" method first developed by Houghten, where potential catalyst synthesis occurs on resin sealed inside porous polypropylene bags (Houghten et al. (1986) *PNAS* 82:5131–5135). Substituents are coupled to the potential catalyst-bearing resins by placing the bags in appropriate reaction solutions, while all common steps such as resin washing and deprotection are performed simultaneously in one reaction vessel. At the end of the synthesis, each bag contains a single potential catalyst moiety.

D) Combinatorial Libraries by Light-Directed, Spatially Addressable Parallel Chemical Synthesis A scheme of combinatorial synthesis in which the identity of a compound is given by its locations on a synthesis substrate is termed a spatially-addressable synthesis. In one embodiment, the combinatorial process is carried out by controlling the addition of a chemical reagent to specific locations on a solid support (Dower et al. (1991) *Annu Rep Med Chem* 26:271–280; Fodor, S. P. A. (1991) *Science* 251:767; Pirrung et al. (1992) U.S. Pat. No. 5,143,854; Jacobs et al. (1994) *Trends Biotechnol* 12:19–26). The spatial resolution of photolithography affords miniaturization. This technique can be carried out through the use protection/deprotection reactions with photolabile protecting groups.

The key points of this technology are illustrated in Gallop et al. (1994) *J Med Chem* 7:1233–1251. A synthesis substrate is prepared for coupling through the covalent attachment of photolabile nitroveratryloxycarbonyl (NVOC) protected amino linkers or ther photolabile linkers. Light is used to selectively activate a specified region of the synthesis support for coupling. Removal of the photolabile protecting groups by light (deprotection) results in activation of selected areas. After activation, the first of a set of amino acid analogs, each bearing a photolabile protecting group on the amino terminus, is exposed to the entire surface. Coupling only occurs in regions that were addressed by light in the preceding step. The reaction is stopped, the plates washed, and the substrate is again illuminated through a second mask, activating a different region for reaction with a second protected building block. The pattern of masks and the sequence of reactants define the products and their locations. Since this process utilizes photolithography techniques, the number of compounds that can be synthesized is limited only by the number of synthesis sites that can be addressed with appropriate resolution. The position of each potential catalyst is precisely known; hence, its interactions with other molecules can be directly assessed.

In a light-directed chemical synthesis, the products depend on the pattern of illumination and on the order of addition of reactants. By varying the lithographic patterns, many different sets of test potential catalysts can be synthesized simultaneously; this characteristic leads to the generation of many different masking strategies.

E) Encoded Combinatorial Libraries

In yet another embodiment, the subject method utilizes a potential catalyst library provided with an encoded tagging system. A recent improvement in the identification of active compounds from combinatorial libraries employs chemical indexing systems using tags that uniquely encode the reaction steps a given bead has undergone and, by inference, the structure it carries. Conceptually, this approach mimics phage display libraries, where activity derives from expressed peptides, but the structures of the active peptides are deduced from the corresponding genomic DNA sequence. The first encoding of synthetic combinatorial libraries employed DNA as the code. A variety of other forms of encoding have been reported, including encoding with sequenceable bio-oligomers (e.g., oligonucleotides and peptides), and binary encoding with additional non-sequenceable tags.

1) Tagging with sequenceable bio-oligomers

The principle of using oligonucleotides to encode combinatorial synthetic libraries was described in 1992 (Brenner et al. (1992) *PNAS* 89:5381–5383), and an example of such a library appeared the following year (Needles et al. (1993) *PNAS* 90:10700–10704). A combinatorial library of nominally $7^7$ (=823,543) peptides composed of all combinations of Arg, Gln, Phe, Lys, Val, D-Val and Thr (three-letter amino acid code), each of which was encoded by a specific dinucleotide (TA, TC, CT, AT, TT, CA and AC, respectively), was prepared by a series of alternating rounds of peptide and oligonucleotide synthesis on solid support. In this work, the amine linking functionality on the bead was specifically differentiated toward peptide or oligonucleotide synthesis by simultaneously preincubating the beads with reagents that generate protected OH groups for oligonucleotide synthesis and protected $NH_2$ groups for peptide synthesis (here, in a ratio of 1:20). When complete, the tags each consisted of 69-mers, 14 units of which carried the code. The bead-bound library was incubated with a fluorescently labeled antibody, and beads containing bound antibody that fluoresced strongly were harvested by fluorescence-activated cell sorting (FACS). The DNA tags were amplified by PCR and sequenced, and the predicted peptides were synthesized. Following such techniques, potential catalyst libraries can be derived for use in the subject method, where the oligonucleotide sequence of the tag identifies the sequential combinatorial reactions that a particular bead underwent, and therefore provides the identity of the potential catalyst on the bead.

The use of oligonucleotide tags permits exquisitely sensitive tag analysis. Even so, the method requires careful choice of orthogonal sets of protecting groups required for alternating co-synthesis of the tag and the library member. Furthermore, the chemical lability of the tag, particularly the phosphate and sugar anomeric linkages, may limit the choice of reagents and conditions that can be employed for the synthesis of non-oligomeric libraries. In preferred embodiments, the libraries employ linkers permitting selective detachment of the test potential catalyst library member for assay.

Peptides have also been employed as tagging molecules for combinatorial libraries. Two exemplary approaches are described in the art, both of which employ branched linkers to solid phase upon which coding and ligand strands are alternately elaborated. In the first approach (Kerr JM et al. (1993) *J Am Chem Soc* 115:2529–2531), orthogonality in synthesis is achieved by employing acid-labile protection for the coding strand and base-labile protection for the ligand strand.

In an alternative approach (Nikolaiev et al. (1993) *Pept Res* 6:161–170), branched linkers are employed so that the coding unit and the test potential catalyst can both be attached to the same functional group on the resin. In one embodiment, a cleavable linker can be placed between the branch point and the bead so that cleavage releases a molecule containing both code and the potential catalyst (Ptek et al. (1991) *Tetrahedron Lett* 32:3891–3894). In another embodiment, the cleavable linker can be placed so that the test potential catalyst can be selectively separated from the bead, leaving the code behind. This last construct is particularly valuable because it permits screening of the test potential catalyst without potential interference of the coding groups. Examples in the art of independent cleavage and sequencing of peptide library members and their corresponding tags has confirmed that the tags can accurately predict the peptide structure.

2) Non-sequenceable tagging: binary encoding

An alternative form of encoding the test potential catalyst library employs a set of non-sequencable electrophoric tagging molecules that are used as a binary code (Ohlmeyer et al. (1993) *PNAS* 90:10922–10926). Exemplary tags are haloaromatic alkyl ethers that are detectable as their trimethylsilyl ethers at less than femtomolar levels by electron capture gas chromatography (ECGC). Variations in the length of the alkyl chain, as well as the nature and position of the aromatic halide substituents, permit the synthesis of at least 40 such tags, which in principle can encode $2^{40}$ (e.g., upwards of $10^{12}$) different molecules. In the original report (Ohlmeyer et al., supra) the tags were bound to about 1% of the available amine groups of a peptide library via a photocleavable o-nitrobenzyl linker. This approach is convenient when preparing combinatorial libraries of peptide-like or other amine-containing molecules. A more versatile system has, however, been developed that permits encoding of essentially any combinatorial library. Here, the potential catalyst would be attached to the solid support via the photocleavable linker and the tag is attached through a catechol ether linker via carbene insertion into the bead matrix (Nestler et al. (1994) *J Org Chem* 59:4723–4724).

This orthogonal attachment strategy permits the selective detachment of library members for assay in solution and subsequent decoding by ECGC after oxidative detachment of the tag sets.

Although several amide-linked libraries in the art employ binary encoding with the electrophoric tags attached to amine groups, attaching these tags directly to the bead matrix provides far greater versatility in the structures that can be prepared in encoded combinatorial libraries. Attached in this way, the tags and their linker are nearly as unreactive as the bead matrix itself. Two binary-encoded combinatorial libraries have been reported where the electrophoric tags are attached directly to the solid phase (Ohlmeyer et al. (1995) PNAS 92:6027–6031) and provide guidance for generating the subject potential catalyst library. Both libraries were constructed using an orthogonal attachment strategy in which the library member was linked to the solid support by a photolabile linker and the tags were attached through a linker cleavable only by vigorous oxidation. Because the library members can be repetitively partially photoeluted from the solid support, library members can be utilized in multiple assays. Successive photoelution also permits a very high throughput iterative screening strategy: first, multiple beads are placed in 96-well microtiter plates; second, ligands are partially detached and transferred to assay plates; third, a metal binding assay identifies the active wells; fourth, the corresponding beads are rearrayed singly into new microtiter plates; fifth, single active potential catalysts are identified; and sixth, the structures are decoded.

F) Selection of Potential Catalysts Based on Thermographic Techniques

In certain embodiments, libraries of potential catalysts will be screened using thermographic techniques (for a recent example of this strategy, see: Taylor and Morken, Science 1998, 280, 267–270). This technology constitutes a general method for the rapid and simultaneous evaluation of each member of large encoded catalyst libraries for the ability to catalyze a given reaction in solution. This technology enables the selection of active catalysts from a library of polymer-bound multifunctional potential catalysts. For example, Taylor and Morken disclosed that from ~7000 beads screened (3150 distinct catalysts), 23 beads were selected for catalysis of an acylation reaction. Their kinetic experiments indicated that the most strongly selected beads were also the most efficient catalysts.

VI. Reaction Conditions

In one aspect of the invention, the subject screening method can be carried out utilizing immobilized potential catalyst libraries. The choice of a suitable polymeric support will be routine to the skilled artisan. In general, the polymeric support will be selected according to at least some of the following criteria: (i) it should not be reactive under conditions used for detecting catalytic activity; and (ii) it will have little to no background catalytic activity. The potential catalysts can be derivatized to the polymeric support utilizing appropriate functional groups and methods known in the art. Those embodiments which employ some form of matrix immobilization of the potential catalyst library are amenable to the use of encoding and/or spatial addressing of the library for later deconvolution.

Insoluble polymeric supports include ftinctionalized polymers based on polystyrene, polystyrene/divinylbenzene copolymers, and other polymers known to the skilled artisan. It will be understood that the polymer support can be coated, grafted, or otherwise bonded to other solid supports.

In another embodiment, the polymeric support can be provided by reversibly soluble polymers. Such polymeric supports include functionalized polymers based on polyvinyl alcohol or polyethylene glycol (PEG). A soluble support can be made insoluble (e.g., can be made to precipitate) by addition of a suitable inert non-solvent. One advantage of reactions performed using soluble polymeric supports is that reactions in solution can be more rapid, higher yielding, and/or more complete than reactions that are performed on insoluble polymeric supports. Accordingly, in preferred embodiments, the polymer support is PEG or PEG-OMe.

In still other embodiments, the potential catalyst library can be synthesized in solution, and by the use of deconvolution techniques, or synthesis in multiple reaction vessels (e.g., microtitre plates and the like), the identity of particular members of the library can be determined.

VII. Catalysts for Stereoselective Nucleophilic Reaction, and Exemplary Uses Thereof As described in further detail below, the subject combinatorial method has been employed to generate a novel class of catalyst useful for, e.g., the addition of a nucleophile across a reactive π-bond.

In general, the invention features a stereoselective nucleophilic addition process which comprises combining a substrate comprising a reactive π-bond, a nucleophile, and at least a catalytic amount of a non-racemic, chiral catalyst of particular characteristics (as described below). The combination is maintained under conditions appropriate for the chiral catalyst to catalyze stereoselective addition of the nucleophile to the reactive π-bond of the substrate. This reaction can be applied to enantioselective processes as well as diastereoselective processes. It may also be adapted for regioselective reactions. Examples follow of enantioselective reactions, kinetic resolution, and regioselective reactions which may be catalyzed according to the present invention.

In an exemplary and preferred embodiment, cyanide ion adds to the carbon of an imine functional group in the presence of the subject chiral, non-racemic catalyst yielding a non-racemic α-amino nitrile product. This embodiment is an example of a subject enantioselective nucleophilic addition reaction, and can be represented by the general transformation:

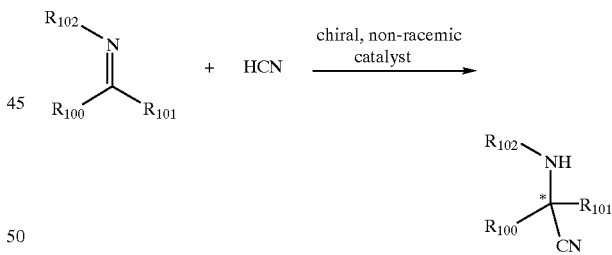

wherein $R_{100}$, $R_{101}$, and $R_{102}$ represent, independently for each occurrence, hydrogen, alkyl, alkenyl, alkynyl, acyl, thioacyl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, amidine, acetal, ketal, aryl, heteroaryl, aziridine, carbamate, epoxide, hydroxamic acid, imide, oxime, sulfonamide, thioamide, thiocarbamate, urea, thiourea, or —$(CH_2)_m$—$R_{80}$, or $R_{102}$, along with the imine carbon and nitrogen, and either $R_{100}$ or $R_{101}$, form a heterocycle (substituted or unsubstituted) having from 4 to 10 atoms, subject to geometric constraints, in the ring structure, or $R_{100}$ and $R_{101}$ together form a ring (substituted or unsubstituted) having from 4 to 10 atoms in the ring structure;

$R_{80}$ represents an unsubstituted or substituted aryl, a cycloalkyl, a cycloalkenyl, a heterocycle, or a polycycle;

m is an integer in the range 0 to 8 inclusive; and

HCN represents hydrogen cyanide or its surrogate, e.g., potassium cyanide, sodium cyanide, acetone cyanohydrin, or trimethylsilyl cyanide.

According to the above reaction scheme, and other reactions and structures recited herein, the designation "*" next to a carbon atom indicates a (potential) chiral center.

The addition of cyanide to imines (the Strecker reaction) constitutes one of the most direct and viable strategies for the asymmetric synthesis of α-amino acid derivatives. Significant progress has been made in the development of stereoselective versions of this reaction using imines bearing covalently attached chiral auxiliaries. However, despite the obvious practical potential of an enantioselective catalytic version of the Strecker reaction, only limited success has been attained to this end. In contrast, as described in the appended examples, we describe herein novel chiral catalysts which catalyze enantioselective Strecker reactions.

In a preferred embodiment, the Strecker catalyst of the present invention is represented by the general formula:

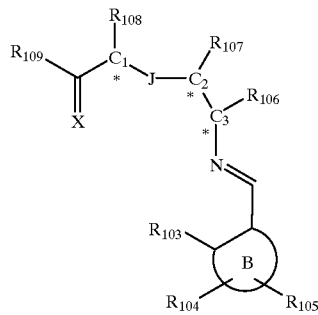

wherein

B represents a monocyclic or polycyclic group (e.g., a cycloalkyl, heterocycle, aromatic or heteroaromatic ring);

$C_1$, $C_2$ and $C_3$ each represent chiral carbon atoms;

X represents O, S or NH;

J represents a linker group including at least one functional group capable of acting as a hydrogen bond donor, e.g., a weak Bronsted acid;

$R_{103}$ represents either a hydrogen bond donor, a Lewis basic group, or a group with both characteristics;

$R_{104}$ represents a sterically bulky, aliphatic or cycloaliphatic substituent of up to 20 carbons (preferably 2–10), e.g., which sterically hinders the Lewis basic group such that it remains disposed in proximity to a catalytic active site including the imine nitrogen of the catalyst and J;

$R_{105}$ is absent, or represents one or more additional substituents of B selected from the group consisting of alkyl, alkenyl, alkynyl, acyl, thioacyl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, amidine, acetal, ketal, aryl, heteroaryl, aziridine, carbamate, epoxide, hydroxamic acid, imide, oxime, sulfonamide, thioamide, thiocarbamate, urea, thiourea, or —$(CH_2)_m$—$R_{80}$; and $R_{106}$ and $R_{107}$ each independently represent alkyl, alkenyl, alkynyl, acyl, thioacyl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, amidine, acetal, ketal, aryl, heteroaryl, aziridine, carbamate, epoxide, hydroxamic acid, imide, oxime, sulfonamide, thioamide, thiocarbamate, urea, thiourea, or —$(CH_2)_m$—$R_{80}$, or $R_{106}$ and $R_{107}$ taken together with $C_2$ and $C_3$ form a ring having from 4 to 8 atoms in the ring;

$R_{108}$ and $R_{109}$ each independently represent an alkyl, represent alkyl, alkenyl, alkynyl, acyl, thioacyl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, amidine, acetal, ketal, aryl, heteroaryl, aziridine, carbamate, epoxide, hydroxamic acid, imide, oxime, sulfonamide, thioamide, thiocarbamate, urea, thiourea, or —$(CH_2)_m$—$R_{80}$, with the proviso that $R_{108}$ and $(C(X)R_{109})$ are not identical (this proviso is implied by the chirality of $C_1$);

$R_{80}$ represents an unsubstituted or substituted aryl, a cycloalkyl, a cycloalkenyl, a heterocycle, or a polycycle; and m is an integer in the range 0 to 8 inclusive.

In preferred embodiments, X is S or O.

In preferred embodiments, $R_{103}$ is —$NH_2$, —OH, or —SH, or a lower alkyl group substituted thereby.

In preferred embodiments, $R_{104}$ is attached to B at a position ortho to $R_{103}$, and meta to the imine substituent. $R_{104}$ is preferably a lower alkyl or alkoxyl group, e.g., a branched lower alkyl such as a t-butyl group.

In preferred embodiments, $R_{106}$ and $R_{107}$ are $C_3$–$C_8$ alkyl groups, or, together with $C_2$ and $C_3$ form a ring having from 4 to 8 atoms in the ring.

In preferred embodiments, J is represented by —NH—Y—NH—, wherein Y is selected from the group consisting of

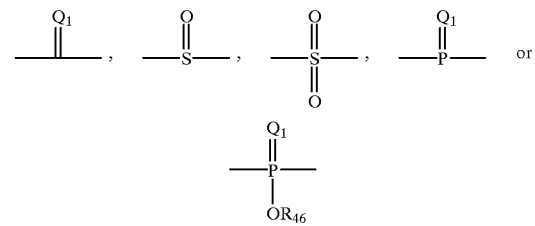

wherein $Q_1$ represents S or O, and $R_{46}$ represents hydrogen, a lower alkyl or an aryl. In more preferred embodiments, Y is selected from the group consisting of —C(=$Q_1$)—, wherein $Q_1$ is O or S.

In certain embodiments, $R_{108}$ represents an alkyl, heteroalkyl, aryl or heteroaryl group.

In preferred embodiments, $R_{108}$ represents a side-chain of a naturally occurring α-amino acid or analog thereof.

In certain embodiments, $R_{109}$ represents an amino group, e.g., a primary or secondary amino group, through preferably a primary amino group. For example, $R_{109}$ can be represented by

wherein $R_9$ and $R_{10}$ each independently represent a hydrogen, an alkyl, an alkenyl, —$(CH_2)_m$—$R_{80}$, or $R_9$ and $R_{10}$ taken together with the N atom to which they are attached complete a heterocycle having from 4 to 8 atoms in the ring structure, or $R_9$ or $R_{10}$ can represent a linker and solid support matrix; $R_{80}$ and m being defined above.

The presence of bulky substituents at one or more of $R_{104}$, $R_{105}$, $R_{106}$, $R_{107}$ and/or $R_{108}$ can have a marked effect on selectivity, and these groups may improve stereochemical communication between the substrate(s) and the catalyst in the transition state.

In preferred embodiments, the Strecker catalyst of the present invention is represented by the general formula:

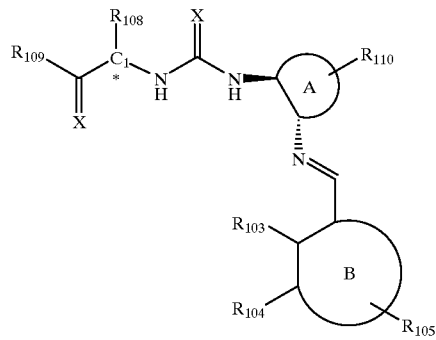

wherein

B, X, $R_{103}$, $R_{104}$, $R_{105}$, $R_{108}$, and $R_{109}$ are defined above;

A represents a monocyclic or polycyclic group (e.g., a cycloalkyl, heterocycle, aryl or heteroaryl ring); and $R_{110}$ is absent, or represents one or more additional substituents of A selected from the group consisting of alkyl, alkenyl, alkynyl, acyl, thioacyl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, amidine, acetal, ketal, aryl, heteroaryl, aziridine, carbamate, epoxide, hydroxamic acid, imide, oxime, sulfonamide, thioamide, thiocarbamate, urea, thiourea, or —$(CH_2)_m$—$R_{80}$.

In preferred embodiments, A is a cycloalkyl having from 3–10 carbon atoms in its ring structure, and more preferably have 5, 6 or 7 carbons in the ring structure.

In additional preferred embodiments, the catalysts of the subject invention are represented by the following general structure:

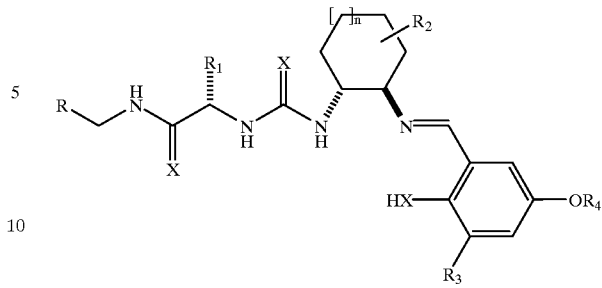

wherein

X represents, independently for each occurrence, O, S, or NR;

R, $R_1$, $R_2$, and $R_3$ represent, independently for each occurrence, H, alkyl, aryl, heteroalkyl, or heteroaryl;

$R_4$ represents H, alkyl, heteroalkyl, aryl, heteroaryl, formyl, or acyl;

$R_2$ is absent or occurs no more than 4 times; and n is an integer selected from the range 0 to 2 inclusive.

In highly preferred embodiments, the general structure above applies:

wherein

X represents, independently for each occurrence, O or S;

R, $R_1$, $R_2$, and $R_3$ represent, independently for each occurrence, H, alkyl, aryl, heteroalkyl, or heteroaryl;

$R_4$ represents alkyl, heteroalkyl, aryl, or heteroaryl;

$R_2$ is absent; and n is an integer selected from the range 0 to 2 inclusive.

In additional highly preferred embodiments, the general structure above applies:

wherein

X represents, independently for each occurrence, O or S;

R, $R_1$, $R_2$, and $R_3$ represent, independently for each occurrence, H, alkyl, aryl, heteroalkyl, or heteroaryl;

$R_4$ represents formyl or acyl;

$R_2$ is absent; and n is an integer selected from the range 0 to 2 inclusive.

In preferred embodiments, the catalysts of the subject invention catalyze at least one stereoselective nucleophilic addition with an enantioselectivity of at least 75% ee, more preferably at least 80% ee, 85% ee, 90% ee, 95% ee or even >98% ee.

The asymmetric Strecker reaction according to the methods of the present invention provides a straightforward entry into enantiomerically enriched α-amino acid derivatives from readily available substrate and catalyst precursors using low catalyst loading. The catalyst is easily prepared on large scale and appears to have an indefinite "shelf life" even when stored under ambient conditions.

In an exemplary embodiment, cyanide ion adds to the carbon of an imine functional group in the presence of a subject chiral, non-racemic catalyst yielding a non-racemic α-amino nitrile product. This embodiment is an example of a subject enantioselective nucleophilic addition reaction. The product of this reaction can be transformed in a single step to non-racemic N-methyl phenylglycine—a non-natural α-amino acid.

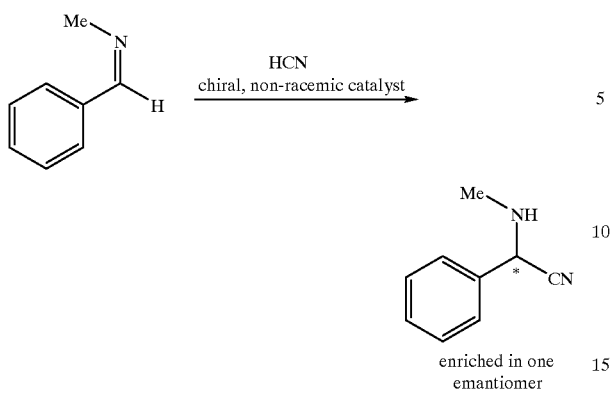

enriched in one emantiomer

To further illustrate, N-allyl-2-naphthylmethanimine can be reacted with HCN to generate the corresponding nitrile, which in turn can be reacted with MeOH in the presence of acid to yield the methyl ester. The allyl group can be subsequently removed with, e.g., dimethylbarbituric acid and catalytic palladium(0), to yield the α-amino ester. Recrystallization can be used to further increase the purity of the single enantiomer.

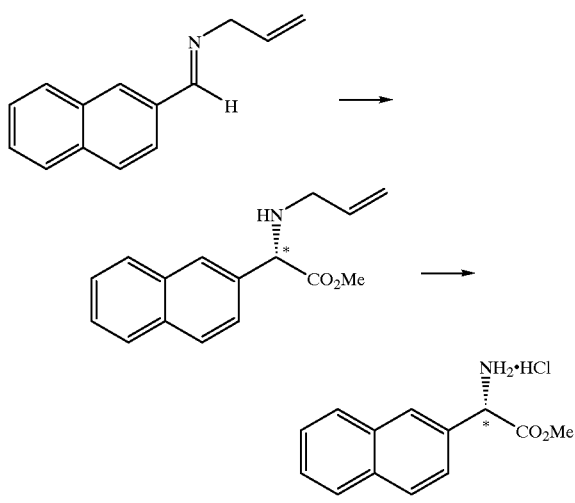

Another illustrative example of the use of the subject catalysts includes the enantioselective conversion of sulfinimines to sulfinamides, e.g., as shown in the reaction scheme below. The resulting sulfinamide can be further converted into a primary amine which contains a new stereogenic center.

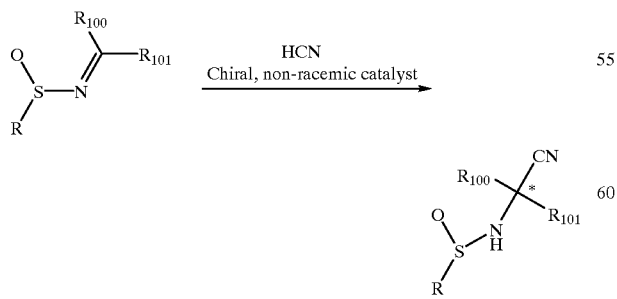

To provide another illustration, the aniline in the reaction shown below (see, e.g., U.S. Pat. No. 5,661,160) is reacted with cyanide in the presence of the subject catalyst to yield a nitrile.

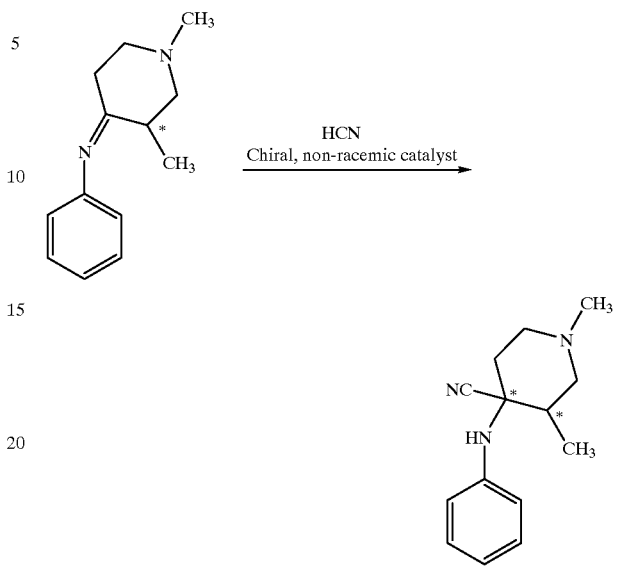

In a further aspect of the present invention, a nucleophile may be added to an endocyclic imine as shown below.

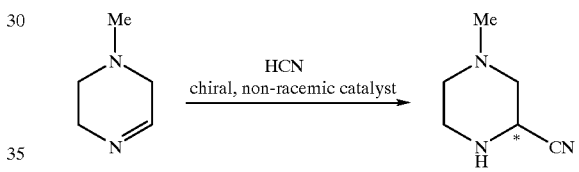

In another aspect of the invention, the nucleophilic addition reaction occurs in a diastereoselective manner in the presence of the subject chiral, non-racemic catalyst. An illustrative example of a diastereoselective reaction of the present invention is shown below.

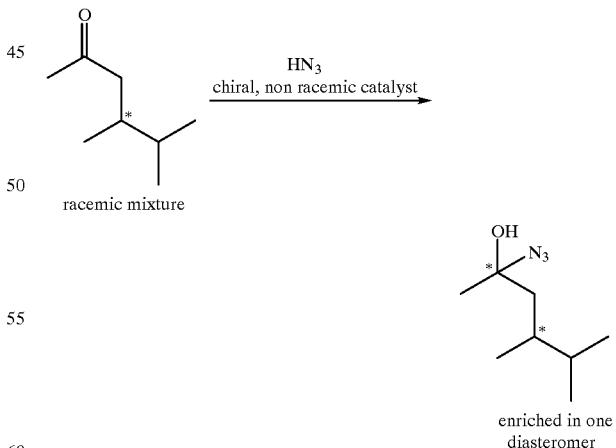

enriched in one diasteromer

In another illustrative embodiment, the present invention provides a method for the kinetic resolution of a racemic mixture of an imine containing an α-stereocenter. In the subject catalyst-mediated kinetic resolution process involving a racemic imine substrate, one enantiomer of the imine can be recovered as unreacted substrate while the other is transformed to the desired product. This aspect of the invention provides methods of synthesizing functionalized non-racemic products from racemic starting materials. This embodiment is a diastereoselective process as well.

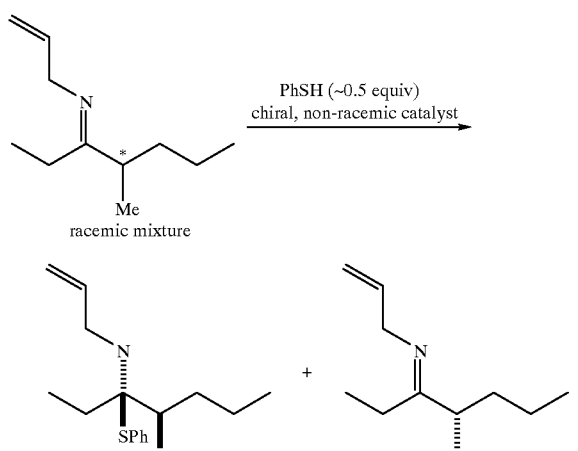

A second type of kinetic resolution possible with the subject catalysts involves the resolution of a racemic nucleophile. The exemplary embodiment shown below centers on the resolution of a racemic mixture of thiols in catalyzed reaction with O-methyl benzophenone oxime. Use of approximately 0.5 equivalents of the oxime ether in the subject method will provide a product mixture comprising both non-racemic unreacted thiol and a non-racemic addition product.

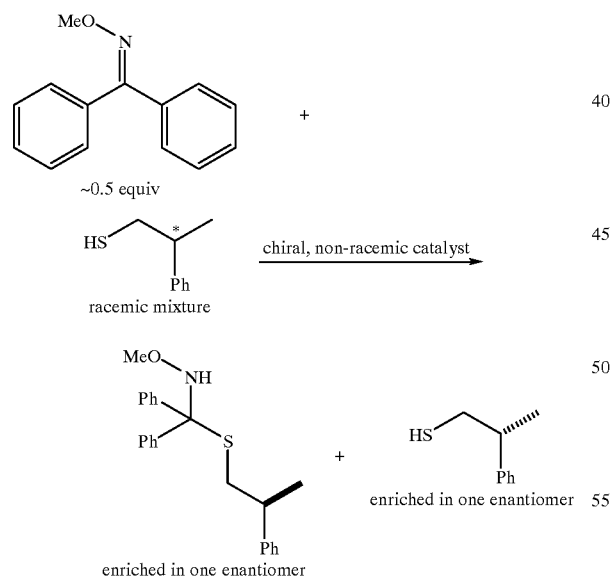

Skilled artisans will recognize that the subject invention can be applied to substrates comprising two reactive π-bonds of differing reactivity. The illustrative embodiment below involves a diamine substrate wherein the imines differ in their steric environments; the subject method is expected, all other factors being equal, to catalyze selectively nucleophilic addition at the less hindered imine moiety.

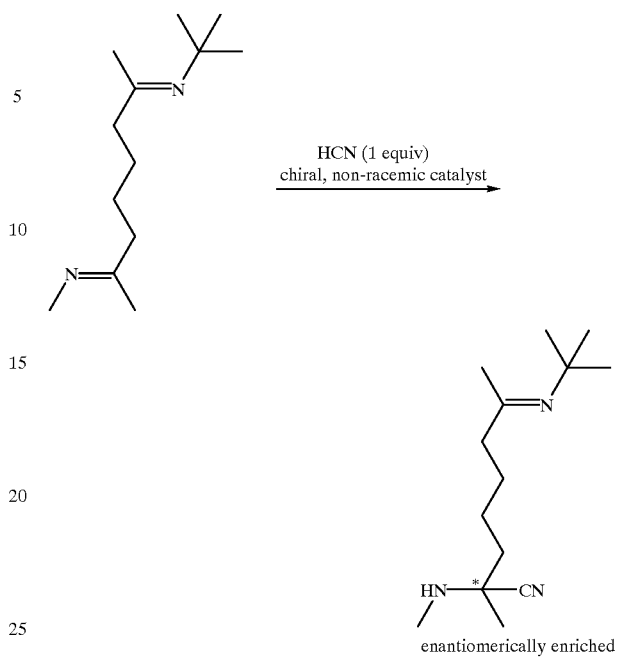

Additionally, skilled artisans will recognize that the subject invention can be applied to substrates comprising different classes of reactive π-bonds. The illustrative embodiment below involves a substrate that comprises both an imine and a hydrazone. The subject method is expected, all other factors being equal, to catalyze nucleophilic addition at the imine moiety.

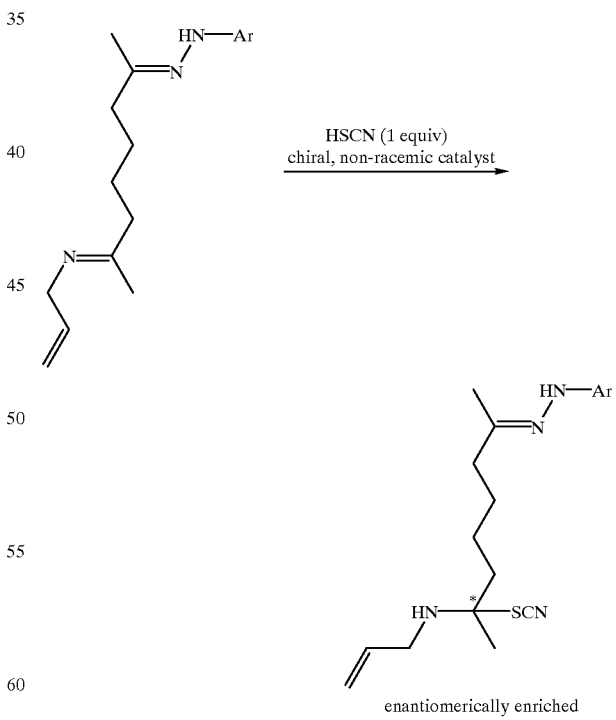

The subject method and catalysts may also be exploited in an intramolecular sense. In the illustrative embodiment that follows, the chiral, non-racemic catalyst may catalyze the intramolecular enantioselective addition of a thiol to an N-allyl imine.

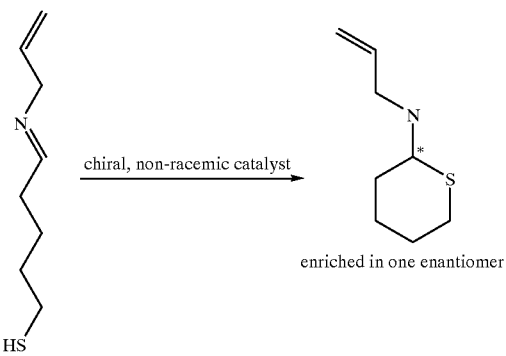

enriched in one enantiomer

The processes of this invention can provide optically active products with very high stereoselectivity (e.g., enantioselectivity or diastereoselectivity) or regioselectivity. In preferred embodiments of the subject enantioselective reactions, enantiomeric excesses of preferably greater than 50%, more preferably greater than 75% and most preferably greater than 90% can be obtained by the processes of this invention. Likewise, with respect to regioselective reactions, molar ratios for desired/undesired regioisomers of preferably greater than 5:1, more preferably greater than 10:1 and most preferably greater than 25:1 can be obtained by the processes of this invention. The processes of this invention can also be carried out at highly desirable reaction rates suitable for commercial use.

As is clear from the above discussion, the chiral products produced by the asymmetric synthesis processes of this invention can undergo further reaction(s) to afford desired derivatives thereof. Such permissible derivatization reactions can be carried out in accordance with conventional procedures known in the art. For example, potential derivatization reactions include epoxidation, ozonolysis, halogenation, hydrohalogenation, hydrogenation, esterification, oxidation of alcohols to aldehydes, ketones and/or carboxylate derivatives, N-alkylation of amides, addition of aldehydes to amides, nitrile reduction, acylation of alcohols by esters, acylation of amines and the like. To further illustrate, exemplary classes of pharmaceuticals which can be synthesized by a scheme including the subject stereoselective reaction are cardiovascular drugs, nonsteroidal antiinflammatory drugs, central nervous system agents, and antihistaminics.

VIII. Exemplification

The invention now being generally described, it will be more readily understood by reference to the following examples which are included merely for purposes of illustration of certain aspects and embodiments of the present invention, and are not intended to limit the invention.

EXAMPLE 1

This example outlines the application of parallel combinatorial library synthesis to the discovery and optimization of a chiral catalyst for the formal addition of hydrogen cyanide to imines (the Strecker reaction). Through an iterative sequence involving the preparation and evaluation of 3 solid phase libraries containing a total of 192 compounds, optimization of reaction enantioselectivity was achieved from an initial lead result of 19% ee up to 91% ee. The catalyst identified through optimization for the hydrocyanation of N-allylbenzaldimine proved effective for a range of imine substrates. In particular, >80% ee was achieved for the first time with any catalyst system for the Strecker reaction of aliphatic imines. The structural features that lead to high enantioselectivity are quite unanticipated, with non-intuitive synergistic effects displayed between catalyst components.

Combinatorial chemistry is now well-recognized as a promising strategy for the discovery and optimization of ligands for biological targets, and it has more recently emerged as a viable approach toward the identification of novel catalysts,[1] coordination complexes,[2] and solid-state materials.[3] Two fundamentally different strategies—split-and-pool, and parallel library synthesis—can be distinguished within combinatorial chemistry, and the choice of method depends on the problem at hand.[4] The split-and-pool strategy may be advantageous when it is desirable or even necessary to evaluate large numbers of compounds because little is known about the target structure and the proportion of compounds with the sought-after activity is likely to be extremely low.[5] The parallel library approach can be most viable for lead optimization, where the basic features of the target structure have already been established.[6] In this case, the greater experimental simplicity associated with screening and identifying spatially arrayed candidate structures can override the possible advantages associated with evaluating larger libraries. We have explored this latter scenario in the context of asymmetric catalysis, with the synthesis of parallel combinatorial libraries of a known class of chiral ligands,[7] and their evaluation as catalysts for the asymmetric hydrocyanation of imines (the Strecker reaction) (eq. 1). In this paper, the viability of the approach is illustrated by the iterative optimization of reaction enantioselectivity from an initial lead result of 19% ee to 91% ee through a sequence of non-obvious modifications in the catalyst structure.

Equation 1

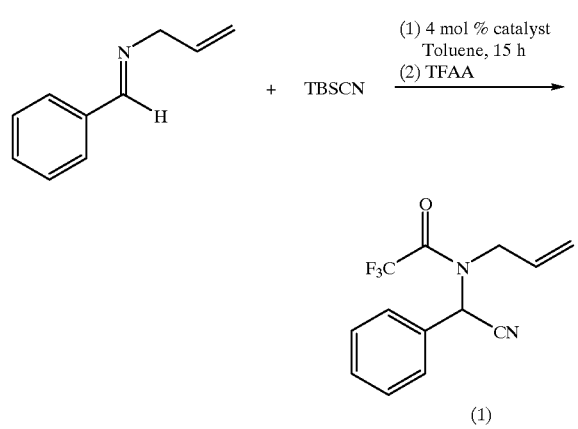

The initial step in the implementation of the parallel catalyst library strategy was the selection of a potential catalyst system that was amenable to solid phase synthesis and systematic structural variation, and also known to be a selective template for chirality transfer. These stipulations dictate high-yielding and generalizable synthetic access to the catalyst with an unobtrusive site for attachment to the solid support. Unfortunately, these criteria are not all met in most of the best known and most effective chiral ligand systems, such as binaphthyl-based ligands, C2 symmetric phosphines, salen ligands, bisoxazolines, and tartrate- and cinchona alkaloid-derived compounds. In contrast, tridentate Schiff base complexes constitute an emerging class of catalysts[8] that might be amenable to solid phase synthesis. These systems are typically comprised of 3 units, a chiral amino alcohol, a salicylaldehyde derivative, and a metal. We chose to modify the core structure such that the amino alcohol was replaced with a diamine, with the second nitrogen on the chiral backbone serving as the site for attachment to the solid support (FIG. 1). An amino acid was incorporated as an additional diversity element between the diamine and the polymer support. The resulting ligand system was evaluated and optimized for the reaction in eq. 1 by carrying out the transformations in parallel with the polymer supported catalysts in individual reaction vessels,[9] and assaying the product mixtures with a commercial autosampler by chiral GC analysis.

Library 1: One ligand of the type in FIG. 1 was prepared and evaluated for catalysis of addition of TBSCN to N-allylbenzaldimine in the presence of a series of different metal ions (see FIG. 2 for the structures of the catalysts of Libraries 1–3). Whereas comparable reactivity was observed in each case, ligand in the absence of any added metal ion proved to be the most enantioselective (19% ee).

Library 2: Based upon this initial lead result, a parallel ligand library of 48 members was prepared and screened in the absence of any added metal ions (see FIG. 3). The amino acid component was observed to exert a very significant effect on reaction enantioselectivity, with leucine-derived catalysts providing the best results. The relative stereochemistry of the catalyst was also important, with (R,R)-diamine-derived catalysts affording substantially higher ee's when coupled with L-leucine than with the unnatural D-leucine enantiomer (e.g. Leu-CH-D: 32% ee; D-Leu-CH-D: 5% ee). Finally, the substituents on the salicylaldehyde derivatives were also found to play a critical role, with t-butyl substituted derivatives A, B, and D affording highest ee's.

At this stage of the development of the catalyst libraries, the linker elements (see FIG. 1) were optimized by a classical, one-catalyst-at-a-time, approach. Control experiments revealed that the caproic acid unit used to link the catalyst to the resin in Libraries 1 and 2 (Linker$_1$) was responsible for a non-negligible level of background reactivity. Direct attachment of the amino acid group of the catalyst to the polystyrene support resulted in improved enantioselectivity for the best catalysts identified from Library 2 (e.g. 30% to 45% ee with Leu-CH-A). The unit used to link the amino acid to the diamine (Linker$_2$) was also found to influence catalyst enantioselectivity. For example, in the Leu-CH-A series, replacement of the urea linker with thiourea led to an enhancement in ee from 45% to 55%, whereas the corresponding guanidine-linked system effected the same Strecker reaction with only 21% ee.

Library 3: On the basis of the results obtained from Library 2, a larger parallel library of 132 thiourea derivatives was prepared incorporating only non-polar L-amino acids and 3-t-butyl substituted salicylaldehyde derivatives. All library members were found to catalyze the reaction in eq. 1, with t-Leu-CH-OMe (OMe denoting 3-t-butyl-5-methoxysalicylaldehyde, D in Library 2) affording the highest enantioselectivity (80% ee, see FIG. 4). The amino acid component was again seen to be crucial, with the bulkiest derivatives (t-Leu, cyclohexylglycine, and isoleucine) providing best results. Interestingly, t-Leu proved to be the best amino acid component for CH-derived catalysts, but the worst one for CP derivatives, effectively highlighting the benefit of evaluating all ligand permutations.

The best catalysts identified from the library screens, t-Leu-CH-OMe (1) and 2, were synthesized independently in solution and tested in the asymmetric reactions in eqs. 2 and 3. With HCN as the cyanide source, the solution-phase catalyst 1 catalyzed the formation of the Strecker adduct of N-allylbenzaldimine in 78% isolated yield and 91% ee at −78° C. Even though 1 was optimized for that particular substrate, it proved to be an effective catalyst for a range of imine derivatives, affording product with moderate-to-high enantioselectivity and yield (Table 1). It is especially noteworthy that aliphatic imine derivatives (Table 1, entries e and f, Table 2, entries 2–4) underwent hydrocyanation with >80% ee. These results constitute the first examples of high enantioselectivity in the Strecker reaction with this important class of substrates.[10]

TABLE 1

| Entry | R | yield(%)[a] | ee(%)[b] |
|---|---|---|---|
| a | Ph | 78 | 91 |
| b | p-OCH$_3$C$_6$H$_4$ | 92 | 70 |
| c | p-BrC$_6$H$_4$ | 65 | 86 |
| d | 2-Napthyl | 88 | 88 |
| e | t-Butyl | 70 | 85 |
| f | Cyclohexyl | 77 | 83 |

[a]Isolated yield.
[b]All ee's were determined by GC or HPLC chromatography using commercial chiral columns. See Supporting Information.

Equation 3

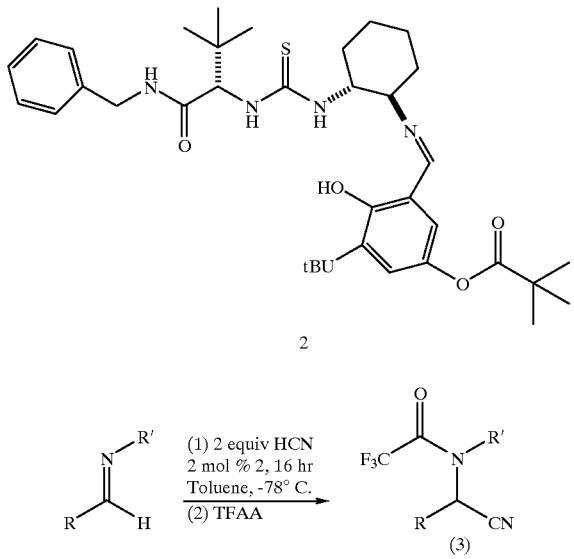

TABLE 2

Results Obtained According to Equation 3.

| Imine | Starting Material | ee of Product (%) |
|---|---|---|
| 1 | N-allylbenzaldimine structure | 95 |

TABLE 2-continued

Results Obtained According to Equation 3.

| Imine | Starting Material | ee of Product (%) |
|---|---|---|
| 2 | N-allyl imine of cyclohexanecarboxaldehyde | 87 |
| 3 | N-allyl imine of pivaldehyde | 95 |
| 4 | N-benzyl imine of pivaldehyde | 95 |

These studies demonstrate that chiral Schiff bases identified from parallel synthetic libraries can be effective asymmetric catalysts for the Strecker reaction. These systems not only exhibit promising enantioselectivity both on solid phase and in solution, but are also easily prepared from inexpensive components. The structural features that lead to high enantioselectivity are quite unanticipated, with non-intuitive synergistic effects displayed between catalyst components. These results raise interesting questions concerning the mechanism of catalysis of the hydrocyanation reaction. Experiments are in progress to address this issue, to further develop this new class of catalysts for the Strecker reaction, and finally to identify effective asymmetric catalysts for other important reactions using this parallel approach.

Notes and References (1) For reviews and discussions, see: (a) Gennari, C.; Nestler, H. P.; Piarulli, U.; Salom, B Liebigs Ann./Recucil 1997, 637. (b) Borman, S. Chem. Eng. News 1996, 74(45), 37.

(2) (a) Francis, M. B.; Finney, N. S.; Jacobsen, E. N. J. Am. Chem. Soc. 1996, 118, 8983. (b) Burger, M. T.; Still, W. C. J. Org. Chem. 1995, 60, 7382. (c) Malin, R.; Steinbrecher, R.; Jannsen, J.; Semmler, W.; Noll, B.; Johannsen, B.; Frommel, C.; H÷hne, W.; Schneider-Mergener, J. J. Am. Chem. Soc. 1995, 117, 11821. (d) Hall, D. G.; Schultz, P. G. Tetrahedron Lett. 1997, 38, 7825. (e) Shibata, N.; Baldwin, J. E.; Wood, M. E. Biorr. Med. Chem. Lett. 1997, 7, 413.

(3) (a) Briceno, G.; Chang, H.; sun, X.; Schultz, P. G.; Xiang, X.-D. Science 1995, 270, 273. (b) Danielson, E.; Golden, J. H.; McFarland, E. W.; Reaves, C. M.; Weinberg, W. H.; Wu, X. D. Nature 1997, 389, 944. (c) Brocchini, S.; James, K.; Tangpasuthadol, V.; Kohn, J. J. Am. Chem. Soc. 1997, 119, 4553. (d) Baker, B. E.; Kline, N. J.; Teado, P. J.; Natan, M. J. J. Am. Chem. Soc. 1996, 118, 8721.

(4) For recent reviews on strategies for the synthesis and evaluation of small-molecule libraries, see: (a) Hobbs DeWitt, S.; Czarnik, A. W. Acc. Chem. Res. 1996, 29, 114. (b) Thomson, L. A.; Ellman, J. A. Chem. Rev. 1996, 96, 555. (c) Armstrong, R. W.; Combs, A. P.; Tempest, P. A.; Brown, S. D.; Keating, T. A. Acc. Chem. Res. 1996, 29, 123. (d) Still, W. C. Acc. Chem. Res. 1996, 29, 155. (e) Terret, N. K.; Gardner, M.; Gordon, D. W.; Kobylecki, R. J.; Steele, J. Tetrahedron 1995, 51, 8135.

(5) See, for example: (a) Combs, A. P.; Kapoor, T. M.; Feng, S.; Chen, J. K.; Daud_-Snow, L. F.; Schreiber, S. L. J. Am. Chem. Soc. 1996, 118, 287. (b) Cheng, Y.; Suenaga, T.; Still, W. C. J. Am. Chem. Soc. 1996, 118, 1813. (c) Liang, R.; Yan, L.; Loebach, J.; Ge, M.; Uozumi, Y.; Sekanina, K.; Horan, N.; Gildersleeve, J.; Thompson, C.; Smith, A.; Biswas, K.; Still, W. C.; Kahne, D. Science 1996, 274, 1520.

(6) See, for example: Kick, E. K.; Roe, D. C.; Skillman, A. G.; Liu, G.; Ewing, T. J. A.; Sun, Y.; Kuntz, I. D.; Ellman, J. A. Chem. Biol. 1997, 4, 297.

(7) For related efforts, see: (a) Burgess, K.; Lim, H.-J.; Porte, A. M.; Sulikowski, G. A. Angew. Chem. Int. Ed. Engl. 1996, 35, 220. (b) Cole, M. B.; Shimizu, K. D.; Krueger, C. A.; Harrity, J. P. A.; Snapper, M. L.; Hoveyda, A. H. Angew. Chem. Int. Ed. Engl. 1996, 35, 1668. Burgess and Sulikowski evaluated libraries of spatially-arrayed metal ligand complexes prepared by combining a series of known ligands with a series of metal ions. Snapper and Hoveyda developed a strategy for the optimization of catalysts synthesized on solid support which they termed "positional scanning", wherein each of the ligand components of the catalyst is optimized in a serial manner. Unlike the combinatorial approach in the present paper wherein every possible ligand permutation is prepared and evaluated, the Snapper-Hoveyda approach results in only a small fraction of the possible ligands being prepared, and as a consequence might miss particularly effective ligand combinations. Nonetheless, their approach has led to the same optimal catalyst structures regardless of the order in which the ligand components are varied.

(8) (a) Aratani, T.; Yoneyoshi, Y.; Nagase, T. Tetrahedron Lett. 1975, 1707. (b) Hayashi, M.; Inoue, T.; Miyamoto, Y.; Oguni, N. Tetrahedron 1994, 50, 4385. (c) Carreira, E. M.; Singer, R. A.; Lee, W. J. Am. Chem. Soc. 1994, 116, 8837. (d) Bolm, C.; Bienewald, F. Angew. Chem. Int. Ed. Engl. 1995, 34, 2641.

(9) Reactions were carried out in 1 mL glass test tubes. Details are provided in the Supporting Information.

(10) (a) Iyer, M. S.; Gigstad, K. M.; Namdev, N. D.; Lipton, M. J. Am. Chem. Soc. 1996, 118, 4910. (b) In independent investigations, we have recently identified Al-based asymmetric catalysts for the Strecker reaction: Sigman, M. S.; Jacobsen, E. N. submitted.

Supporting Information

General: 100–200 μm aminomethylated polystyrene (0.44 mmol/g) was purchased form Novabiochem and rinsed with DMF, THF, and toluene before use. Fmoc-amino acids were purchased from Advanced Chemtech and used as received. TMSCN was purchased from Aldrich and distilled before use. TBSCN was purchased from Aldrich and used as received. (R,R)-1,2-Diaminocyclohexanel and (R,R)-diphenyl-1,2-ethylenediamine[2] were resolved by literature methods. CP was synthesized by a literature method.[3] Salicylaldehydes were synthesized according to published procedures.[1] For library 1 (linker/urea), the aminomethylated polystyrene was derivatized with 6-aminocaproic acid using procedures b and c (below). All coupling reactions were carried out in fritted 1.5 mL or 10 mL disposable chromatography columns. Reactions were filtered upon completion and rinsed with DMF, THF, CH$_2$Cl$_2$ and toluene unless otherwise indicated. The progress of all amino acid coupling reactions was monitored by the UV quantification of dibenzofulvene released from 2 mg resin samples upon Fmoc cleavage. Thiourea and urea formation were monitored by IR for disappearance of isothiocyanate and p-nitrophenyl carbamate bands.

Solid Phase Urea Library Synthesis:

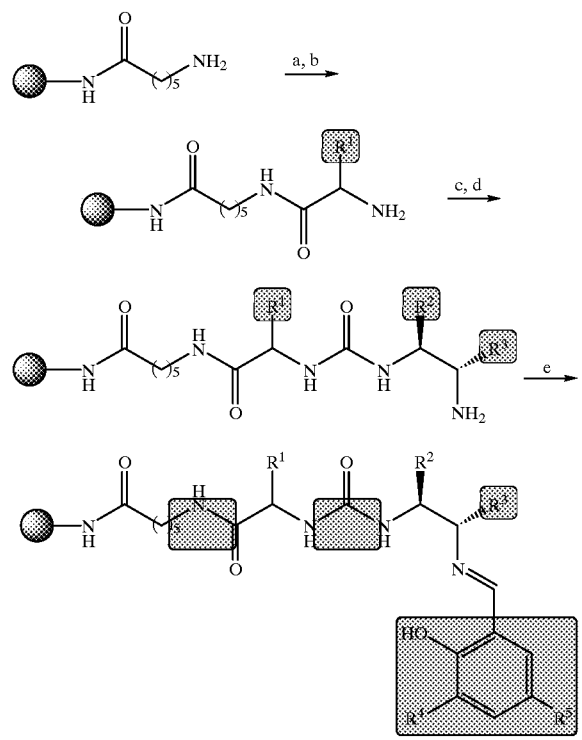

Synthesis Outline: (a) Library split into appropriate number of vials. (b) 2.5 eq Fmoc-amino acid, 2.5 eq HBTU, 5 eq DIPEA, 2.5 eq HOBT, DMF, 2h. (c) 30% piperdine in DMF, 30 min. (d) 0.5 M p-nitrophenyl chloroformate, 0.5 M DIPEA, THF/CH$_2$Cl$_2$ (1/1, v/v), 30 min (rinsed with THF and CH$_2$Cl$_2$ only).[4] (e) 0.5 M Diamine, TEA, DMF, 3h. (f) aldehyde, DMF, 1h.

Solid Phase Thiourea Library Synthesis:

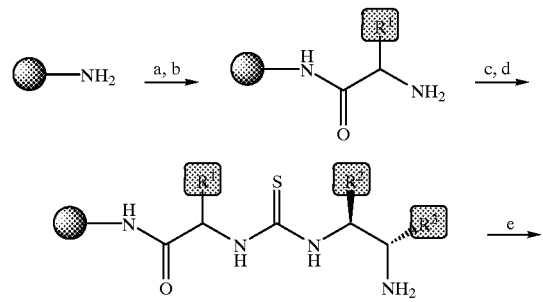

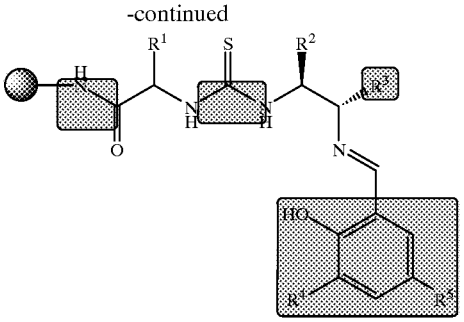

Synthesis Outline: (a) Library split into appropriate number of vials. (b) 2.5 eq Fmoc-amino acid, 2.5 eq HBTU, 5 eq DIPEA, 2.5 eq HOBT, DMF, 2h. (c) 30% piperdine in DMF, 30 min. (d) 0.5 M thiocarbonyl diimidazole, THF, 30 min (rinsed with THF and CH$_2$Cl$_2$ only). (e) 0.5 M Diamine, TEA, DMF, 3h. (f) aldehyde, DMF, 1h.

Formation of Solid Phase Metal Complexes:

Using Leu-CH-A as a representative library member, the resin was suspended in a 0.1 M solution of the metal source and agitated for the length of time specified in Table 1. The resin was rinsed with THF, CH$_2$Cl$_2$, toluene followed by drying under reduced pressure. Incorporation of metal was tested by staining with either 1-nitroso-2-naphthol (NNP) or pyrocatechol violet (PCV) (Table 1).

TABLE 1

Conditions and staining of metal insertions into Leu-CH-A.

| Metal Source | Solvent (time) | Color | Stain (color) |
|---|---|---|---|
| Zn(OTf)$_2$/2,6-lutidine | THF (4 h) | Light yellow | PCV (blue) |
| Ti(OiPr)$_4$ | Toluene (4 h) | Yellow | PCV (blue) |
| Zr(OiPr)$_4$ | THF (12 h) | Yellow | PCV (red) |
| Yb(OTf)$_3$/2,6-lutidine | THF (12 h) | Yellow | PCV (red) |
| Fe(acac)$_3$ | THF (12 h) | Green | PCV (red) |
| Rh(acac)$_3$ | THF (12 h) | Purple | No test |
| Co(OAc)$_2$/2,6-lutidine | EtOH (12 h) | Brown | NNP (orange) |
| Cu(acac)$_2$ | THF (4 h) | Green/blue | PCV (green) |
| Gd(OTf)$_3$/2,6-lutidine | 10% MeOH/THF (5 h) | Yellow | PCV (red) |
| Nd(OTf)$_3$/2,6-lutidine | 10% MeOH/THF (5 h) | Yellow | PCV (red) |
| MnCl$_2$/2,6-lutidine | 10% MeOH/THF (5 h) | brown | PCV (green) |

Screening of the Strecker Reaction:

In 500 μL test tubes, 1 mg of resin (one library member per vial, 4.4 mol %), 50 μL of a 200 mM solution of imine in toluene and 50 μL of a 250 mM solution of TBSCN in toluene were combined. Each vial was sealed with a rubber septum and agitated for 15 h. After this time, a 20 μL aliquot was quenched in a 400 μL solution of trifluoroacetic anhydride (100 mM) in dichloroethane. Conversions and enantioselectivities were determined by autosampling GC equipped with a 20 m×0.25mm γ-TA chiral column (Advanced Seperations Technologies inc., 37 Leslie Ct, P. O. Box 297, Whippany, N.J. 07981, 110° C. isothermal, 25 min).

Synthesis of Solution Phase Catalyst:

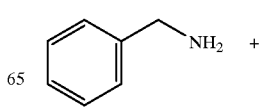

-continued

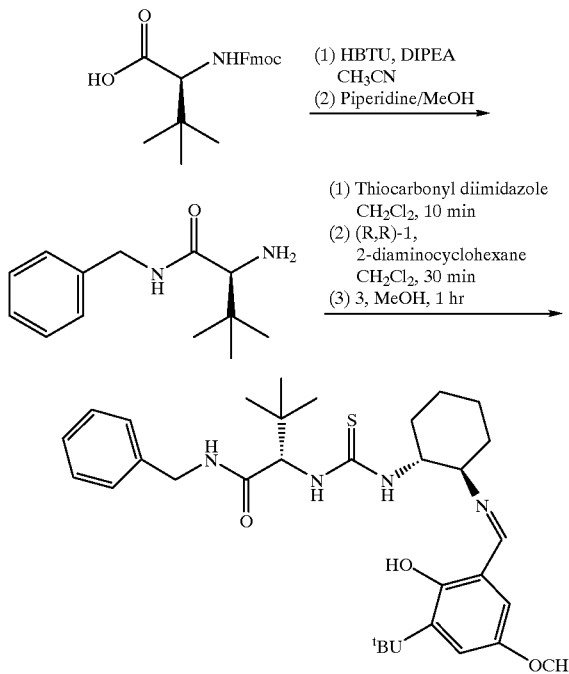

(Benzyl-t-Leu): To a solution of 500 mg of Fmoc-tert-Leucine (1.41 mmol) and 0.54 mL of DIPEA (3.11 mmol, 2.2 equiv) in acetonitrile, 590 mg of HBTU (1.55 mmol, 1.1 equiv) was added. After 1 min, 309 μL of benzyl amine (2.82 mmol, 2.0 equiv) was added and the reaction stirred for 30 min. The mixture was partitioned between $CHCl_3$ (50 mL) and $H_2O$ (50 mL). The organic phase was washed with $H_2O$ (2×50 mL), dried over $Na_2SO_4$, and concentrated in vacuo. The resulting residue was filtered through a short plug of silica eluting with 4% $MeOH/CH_2Cl_2$. The solvent was removed in vacuo and the residue was dissolved in 10 mL 1:1 piperdine/MeOH, stirred for 30 min and partitioned between 50 mL of $CHCl_3$ and 25 mL $H_2O$. The organic phase was washed with $H_2O$(25 mL), dried over $Na_2SO_4$ and concentrated in vacito. Purification by silica gel chromatography (5% $MeOH/CH_2Cl_2$) afforded 242 mg of a white solid (78% yield, 2 steps): mp 53–54° C.; IR (KBr) 3303, 1650 $cm^{-1}$; $^1H$ NMR (400 MHz, $CDCl_3$) δ 7.33 (m, 5H), 7.05 (s, 1H), 4.45 (d, j=0.9 Hz, 1H), 4.43 (d, J=0.9 Hz, 1H), 3.14 (s, 1H), 1.41 (s, 2H), 1.01 (s, 9H); $^{13}C$ NMR {$^1H$} (100 MHz, $CDCl_3$) δ 173.4, 138.5, 128.5, 127.8, 127.3, 64.3, 43.0, 34.1, 26.7; HRMS (M+H) calcd 221.1654, obsd 221.1658.

Benzyl-t-Leu-CH-3 (1): To a 0° C. solution of 45 mg of thiocarbonyl diimidazole (0.255 mmol, 1.1 equiv) in 2 mL of $CH_2Cl_2$ was added a precooled solution of Benzyl-t-Leu (51 mg, 0.232 mmol) in 2 mL of $CH_2Cl_2$ over 1 min. After 10 min, the solution was filtered through a short plug of silica, eluting with $CH_2Cl_2$. The solvent was concentrated to ca. 2 mL and added slowly to a stirring solution of (R,R)-1,2-diaminocyclohexane (132 mg, 1.16 mmol, 5 eq) in 1 mL of $CH_2Cl_2$. After 30 min, the reaction mixture was partitioned between $CH_2Cl_2$ (20 mL) and $H_2O$ (20 mL). The organic layer was washed with $H_2O$ (2×20 mL), dried over $Na_2SO_4$ and concentrated by reduced pressure. A NMR of the resulting residue showed a mixture of two main products. This mixture was dissolved in 2 mL of MeOH, treated with 24 mg of 3 (0.114 mmol) and allowed to stir for 1 hr. The solvent was removed in vacuo and the resulting residue was purified by silica gel chromatography (1% MeOH/$CH_2Cl_2$) affording a yellow solid in 18% overall yield (3 steps): recrystallized from benzene/hexane (1:3); mp 115° C. (dec); IR (KBr) 330, 2942, 1649, 1535 $cm^{-1}$; $^1H$ NMR (400 MHz, $CDCl_3$) δ 13.80 (s, 1H), 8.18 (s, 1H), 7.20 (d, J=2.9 Hz, 1H), 7.05 (m, 4H), 6.99 (m, 1H), 6.85 (br, 1H), 6.68 (d, J=2.9 Hz, 1H), 6.20 (br, 1H), 5.56(br, 1H), 5.01 (br, 1H), 4.29 (dd, J=6.4, 15 Hz, 1H), 4.07 (br, 1H), 3.87 (dd, J=5.1 HZ, 1H), 3.50 (br, 3H), 2.99 (br, 1H), 1.91 (s, 1H), 1.58 (s, 9H), 1.58–1.01 (m, 5H), 0.97 (s, 9H); $^{13}C$ NMR {$^1H$} (100 MHz, $CDCl_3$) δ 170.7, 165.7, 154.8, 151.2, 138.9, 137.6, 128.7, 127.9, 127.8, 127.6, 118.6, 118.0, 111.8, 77.2, 66.5, 57.1, 55.9, 43.6, 35.0, 34.8, 32.9, 31.1, 29.3, 26.8, 24.0, 23.4; HRMS m/z (M+Na) calcd 589.3188, obsd 589.3183. Solution Phase Catalyst Screening: In a flamed dried 10 mL round bottom flask, 1 (1.8 mg, 3.5 μmol, 2 mol %), imine (25 mg, 0.17 mmol) and 0.7 mL of toluene were combined. The reaction was cooled to −78° C. and 125 μl of a 2.8 M solution of HCN (2 equiv) in toluene was added. After stirring for 24 h, the reaction was quenched with TFAA (2 equiv) and warmed to ambient temperature. The solvent was removed in vacuo and the resulting was purified as and analyzed as described below.

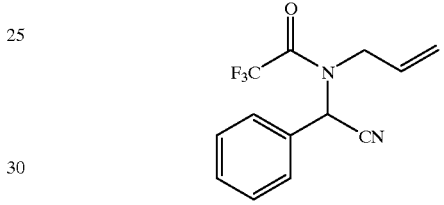

(10a): Product was obtained in 78% yield as a clear oil after purification N by flash chromatography (3:2 hexanes:$CH_2Cl_2$) and in 91% ee by Chiral GC analysis (γ-TA, 110° C. isothermal, $t_r$(major)=21.7 min, $t_r$(minor)=24.5 min); IR (thin film) 2936, 2249, 1701$cm^{-1}$; $^1H$ NMR (400 MHz, $CDCl_3$) δ 7.45 (m, 5H), 6.65 (s, 1H), 5.66 (m, 1H), 5.19 (d, J=10.2 Hz, 1H), 5.13 (d, J=17.0 Hz, 1H) 4.15 (dd, J=4.7, 17.0 Hz, 1H), 3.91 (dd, J=6.0, 17.0 Hz, 1H); $^{13}C$ NMR {$^1H$} (100 MHz, $CDCl_3$) δ 157.9 (q, J=38 Hz),131.1, 130.1, 130., 129.4, 127.8, 120.3, 117.5 (q, J=288 Hz), 115.2, 49.8, 48.6; HRMS m/z (M+$NH_4^+$) calcd 286.1167, obsd 286.1163.

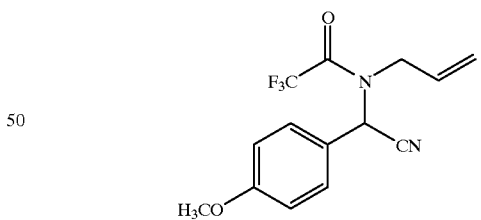

(10b): Product was obtained in 92% yield as a clear oil after purification by flash chromatography (3:2 hexanes:$CH_2Cl_2$) and in 70% ee by Chiral HPLC analysis (Chiralcel AS, 5% IPA/Hexanes, 1 mL./min, $t_r$(major)=9.7 min, $t_r$(minor) 11.5 min; IR (thin film) 2940, 1701, 1613 $cm^{-1}$; $^1H$ NMR (400 MHz, $CDCl_3$) δ 7.36 (d, J=8.6 Hz, 2H), 6.94 (d, J=8.6 Hz, 2H), 6.57 (s, 1H), 5.65 (m, 1H), 5.19 (d, J=10.2 Hz, 1H), 5.14 (d, J=17.2 Hz, 1H) 4.15 (dd, J=4.2, 17.0 Hz, 11), 3.87 (dd, J=6.2, 17.0 Hz, 1H), 3.83 (s, 3H); $^{13}C$ NMR {$^1H$} (100 MHz, $CDCl_3$) δ 160.9, 157.8 (q, J=38 Hz), 131.4, 129.5, 121.9, 120.1, 117.5 (q, J=288 Hz), 115.6, 114.8, 55.5, 49.448.3; HRMS m/z ($M^+$) calcd 298.0929, obsd 298.0936.

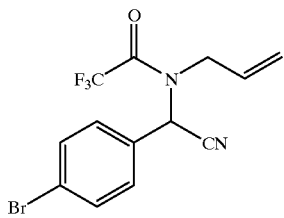

(10c): Product was obtained in 65% yield as a clear oil after purification by flash chromatography (3:2 hexanes:$CH_2Cl_2$) and in 86% ee by Chiral HPLC analysis (Chiralcel AS, 5% IPA/Hexanes, 1 mL./min, $t_r$(major)=6.2 min, $t_r$(minor)=8.1 min); IR (thin film) 2936, 1701 $cm^{-1}$; $^1$H NMR (400 MHz, $CDCl_3$) δ 7.56 (d, J=8.4 Hz, 2H), 7.31 (d, J=8.4 Hz, 2H), 6.52 (s, 1H), 5.65 (m, 1H), 5.21 (d, J=10.2 Hz, 1H), 5.15 (d, J=17.1 Hz, 1H), 4.15 (dd, J=5.5, 17.0 Hz, 1H), 3.92 (dd, J=6.3, 17.0 Hz, 1H); $^{13}$C NMR {$^1$H} (100 MHz, $CDCl_3$) δ 157.7, 132.7, 131.0, 129.5, 124.5, 120.8, 117.4, 114.8, 114.5, 49.6, 49.0; HRMS m/z ($M^+$) calcd 345.9929, obsd 345.9931.

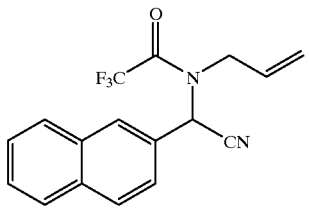

(10d): Product was obtained in 88% yield as a white solid after purification by flash chromatography (3:2 hexanes:$CH_2Cl_2$) and in 88% ee by Chiral HPLC analysis (Chiralcel AS, 5% IPA/Hexanes, 1 mL./min, $t_r$(major)=7.0 min, $t_r$(minor)=8.4 min). mp 72–73° C.; IR (thin film) 3061, 2934, 1701 $cm^{-1}$ $^1$; $^1$H NMR (400 MHz, $CDCl_3$) δ 8.06 (s, 1H), 7.90 (m, 3H), 7.59 (m, 2H), 7.37 (m, 1H) 6.85 (s, 1H), 5.69 (m, 1H), 5.17 (d, J=10.4 Hz,1H), 5.12(d, J=17.2 Hz, 1H), 4.20 (dd, J=4.9, 17.0 Hz, 1H), 3.50 (dd, J=6.5, 17.0 Hz, 1H); $^{13}$C NMR {$^1$H} (100 MHz, $CDCl_3$) δ 157.9 (q, J=38 Hz), 133.6, 132.9, 131.2, 129.8, 128.3, 128.1, 127.9, 127.7, 127.4, 124.2, 120.4, 117.6 (q, J=287 Hz), 115.4, 114.7, 50.0, 48.6; HRMS m/z ($M^+$) calcd 318.0980, obsd 318.0974.

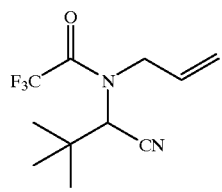

(10e): Product was obtained in 70% yield as a clear oil after purification by flash chromatography (3:2 hexanes:$CH_2Cl_2$) and in 85% ee by Chiral GC analysis (γ-TA, 112° C. isothermal, $t_r$(major)=4.0 min, $t_r$(minor)=6.0 min); IR(thin film) 2972, 1705 $cm^{-1}$; $^1$H NMR (400 MHz, $CDCl_3$) δ 5.87 (m, 1H), 5.33 (d, J=10.4 Hz, 1 H), 5.25 (d, J=17.2 Hz, 1H), 4.25 (s(br), 2H), 1.16 (s, 9H); $^{13}$C NMR {$^1$H} (100 MHz, $CDCl_3$) δ 157.5 (J=37 Hz), 132.0, 119.0, 117.4 (q, J=286 Hz), 115.3, 56.7, 40.5, 38.1, 26.9; HRMS m/z ($M+NH_4^+$) calcd 266.1480, obsd 266.1481.

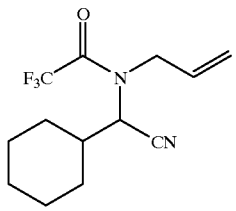

(10f): Product was obtained in 77% yield as a clear oil after purification by flash chromatography (3:2 hexanes:$CH_2Cl_2$) and in 83% ee by Chiral GC analysis (γ-TA, 120° C. isothermal, $t_r$(major)=13.6 min, $t_r$(minor)=15.6 min); IR (thin film) 2936, 2859, 1704 $cm^{-1}$; $^1$H NMR (400 MHz, $CDCl_3$) δ 5.85 (m, 1H), 5.38 (d, J=15.7 Hz, 1H), 5.35 (d, J=9.8 Hz, 1H), 4.65 (d, j=10.6 Hz, 1H), 4.26 (dd, J=4.9, 16.9 Hz, 1H) 4.26 (dd, J=6.9, 16.9 Hz, 1H), 2.09 (m, 2H), 1.84–1.60 (m, 4H), 1.40–0.85 (m, 5H); $^{13}$C NMR {$^1$H} (100 MHz, $CDCl_3$) δ 157.8 (j=37 Hz), 131.6, 120.6, 117.4 (q, J=286 Hz), 115.9, 53.6, 50.4, 38.3, 30.0, 28.9, 25.7, 25.3, 25.1; HRMS m/z ($M+NH_4^{+)\ calcd}$ 292.1637, obsd 292.1625. Absolute Configuration Determination: Racemic and (R)-phenylglycine were converted to their methyl esters[5] and allylated with allyl acetate (Pd-catalyzed).[6] Analysis of the trifluoroacetamide of the product by Chiral GC (γ-TA isothermal 112° C.) gave retention times of 36.0 (R) and 37.62 (S). Asymmetric Strecker reaction product was hydrolyzed to the allyl amino acid methyl ester. Chiral GC analysis showed the major enantiomer to be (S). The other compounds were assigned by analogy to be (S) amino nitriles.

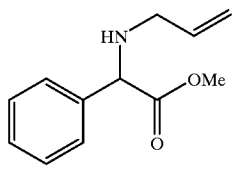

IR (thin film) 3338, 1738 $cm^{-1}$; $^1$H NMR (400 MHz, $CDCl_3$) δ 7.34 (m, 5H), 5.88 (ddd, J=6.1, 10.1, 17.2 Hz, 1H), 5.17 (dd, J=1.6, 17.2 Hz, 1H), 5.12 (dd, J=1.3, 10.1 Hz, 1H)), 4.41 (s, 1H), 3.69 (s, 3H), 3.21 (dd, J=6.1, 1.0 Hz, 1H), 3.19 (dd, J=6.1, 1.0 Hz, 1H); $^{13}$C NMR {$^1$H} (100 MHz, $CDCl_3$) δ 173.3, 137.9, 135.9, 128.7, 128.0, 127.4, 116.7, 64.3, 52.1, 50.0; HRMS m/z (M+H) calcd 206.1181, obsvd 206.1174.

(1) Larrow, J. F.; Jacobsen, E. N.; Gao, Y.; Hong, Y.; Nic, X.; Zepp, C. M. *J. Org. Chem.* 1994, 59, 1939.
(2) Pikul, S.; Corey, E. *J. Org. Synth.* 71, 22.
(3) Reddy, D. R.; Thorton, E. R. *J Chem. Soc. Commun.* 1992, 172.
(4) (a) Hutchins, S. M.; Chapman, K. T. *Tetrahdron Lett.*, 1994, 35, 4055. (b) Hutchins, S. M.; Chapman, K. T. *Tetrahedron Lett.*, 1995, 36, 2583.
(5) Bodanszky, M.; Bodanszky, A. *The Practice of Peptide Synthesis* Springer-Verlag: New York, 1994, p30.
(6) Takahashi, K.; Miyake, A.; Hata, G. *Bull. Chem. Soc. Japan* 1972, 45, 230.

All of the references and publications cited herein are hereby incorporated by reference.

Equivalents

Those skilled in the art will recognize, or be able to ascertain using no more than routine experimentation, numerous equivalents to the specific polypeptides, nucleic acids, methods, assays and reagents described herein. Such equivalents are considered to be within the scope of this invention.

We claim:

1. A catalyst represented by the following structure:

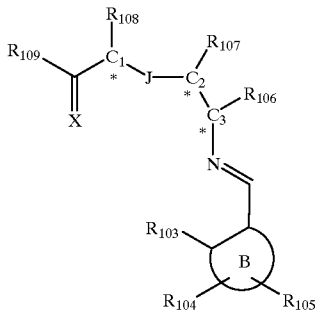

wherein

B represents an optionally substituted aromatic or heteroaromatic group;

$C_1$, $C_2$ and $C_3$ each represent chiral carbon atoms;

X represents O, S or NH;

J represents a linker group with 2–6 heavy atoms in its backbone including at least one functional group capable of acting as a hydrogen bond donor;

$R_{103}$ represents either a hydrogen bond donor, a Lewis basic group, or a group with both characteristics;

$R_{104}$ represents an aliphatic or cycloaliphatic substituent of up to 20 carbons (preferably 2–10);

$R_{105}$ is absent, or represents one or more additional substituents of B selected from the group consisting of alkyl, alkenyl, alkynyl, acyl, thioacyl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, amidine, acetal, ketal, aryl, heteroaryl, aziridine, carbamate, epoxide, hydroxamic acid, imide, oxime, sulfonamide, thioamide, thiocarbamate, urea, thiourea, or —$(CH_2)_m$—$R_{80}$; and $R_{106}$ and $R_{107}$ each independently represent alkyl, alkenyl, alkynyl, acyl, thioacyl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, amidine, acetal, ketal, aryl, heteroaryl, aziridine, carbamate, epoxide, hydroxamic acid, imide, oxime, sulfonamide, thioamide, thiocarbamate, urea, thiourea, or —$(CH_2)_m$—$R_{80}$, or $R_{106}$ and $R_{107}$ taken together with $C_2$ and $C_3$ form a ring having from 4 to 8 atoms in the ring;

$R_{108}$ and $R_{109}$ each independently represent an alkyl, represent alkyl, alkenyl, alkynyl, acyl, thioacyl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, amidine, acetal, ketal, aryl, heteroaryl, aziridine, carbamate, epoxide, hydroxamic acid, imide, oxime, sulfonamide, thioamide, thiocarbamate, urea, thiourea, or —$(CH_2)_m$—$R_{80}$, with the proviso that $R_{108}$ and $(C(X)R_{109})$ are not identical (this proviso is implied by the aforementioned chirality of $C_1$);

$R_{80}$ represents an unsubstituted or substituted aryl, a cycloalkyl, a cycloalkenyl, a heterocycle, or a polycycle; and m is an integer in the range 0 to 8 inclusive.

2. A catalyst according to claim 1, wherein X is S or O.

3. A catalyst according to claim 1, wherein there is a 1,2-positional relationship between $R_{104}$ and $R_{103}$, and there is a 1,3-positional relationship between $R_{104}$ and the imine substituent on B.

4. A catalyst according to claim 1, wherein $R_{104}$ is a lower alkyl or alkoxyl group.

5. A catalyst according to claim 1, wherein $R_{106}$ and $R_{107}$ are $C_3$–$C_8$ alkyl groups, or, together with $C_2$ and $C_3$ form a ring having from 4 to 8 atoms in the ring.

6. A catalyst according to claim 1, wherein $R_{108}$ represents an alkyl, heteroalkyl, aryl or heteroaryl group.

7. A catalyst according to claim 1, wherein $R_{108}$ represents a side-chain of a naturally occurring α-amino acid or analog thereof.

8. A catalyst according to claim 7, wherein $R_{109}$ represents an amino group.

9. A catalyst represented by the following structure:

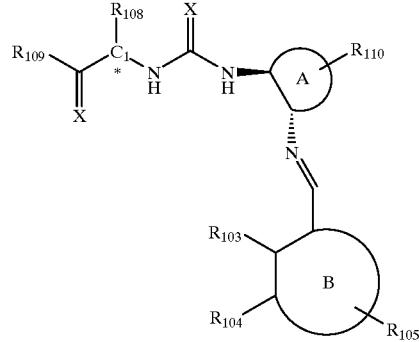

wherein

A represents an optionally substituted ring having from 4 to 8 atoms in the ring;

B represents an optionally substituted aromatic or heteroaromatic group;

$C_1$ represents a chiral carbon atom;

X represents O, S or NH;

$R_{103}$ represents either a hydrogen bond donor, a Lewis basic group, or a group with both characteristics;

$R_{104}$ represents an aliphatic or cycloaliphatic substituent of up to 20 carbons;

$R_{105}$ is absent, or represents one or more additional substituents of B selected from the group consisting of alkyl, alkenyl, alkynyl, acyl, thioacyl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, amidine, acetal, ketal, aryl, heteroaryl, aziridine, carbamate, epoxide, hydroxamic acid, imide, oxime, sulfonamide, thioamide, thiocarbamate, urea, thiourea, or —$(CH_2)_m$—$R_{80}$; and $R_{108}$ and $R_{109}$ each independently represent an alkyl, represent alkyl, alkenyl, alkynyl, acyl, thioacyl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, amidine, acetal, ketal, aryl, heteroaryl, aziridine, carbamate, epoxide, hydroxamic acid, imide, oxime, sulfonamide, thioamide, thiocarbamate, urea, thiourea, or —$(CH_2)_m$—$R_{80}$, with the proviso that $R_{108}$ and $(C(X)R_{109})$ are not identical (this proviso is implied by the aforementioned chirality of $C_1$);

$R_{110}$ is absent, or represents one or more additional substituents of A selected from the group consisting of alkyl, alkenyl, alkynyl, acyl, thioacyl, alkylthio, imine, amide, phosphoryl, phosphonate, phosphine, carbonyl, carboxyl, carboxamide, anhydride, silyl, thioalkyl, alkylsulfonyl, arylsulfonyl, selenoalkyl, ketone, aldehyde, ester, heteroalkyl, amidine, acetal, ketal, aryl, heteroaryl, aziridine, carbamate, epoxide, hydroxamic acid, imide, oxime, sulfonamide, thioamide, thiocarbamate, urea, thiourea, or —$(CH_2)_m$—$R_{80}$, $R_{80}$ represents an unsubstituted or substituted aryl, a cycloalkyl, a cycloalkenyl, a heterocycle, or a polycycle; and m is an integer in the range 0 to 8 inclusive.

10. A catalyst according to claim 7, wherein A is a cycloalkyl having 5, 6 or 7 carbons in the ring structure.

11. A catalyst represented by the following formula:

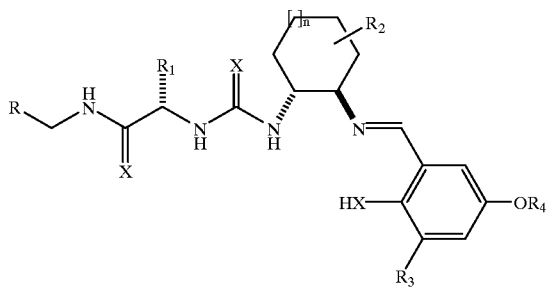

wherein

X represents, independently for each occurrence, O, S, or NR;

R, $R_1$, $R_2$, and $R_3$ represent, independently for each occurrence, H, alkyl, aryl, heteroalkyl, or heteroaryl;

$R_4$ represents H, alkyl, heteroalkyl, aryl, heteroaryl, formyl, or acyl;

$R_2$ is absent or occurs no more than 4 times; and n is an integer selected from the range 0 to 2 inclusive.

12. A catalyst according to claim 11, wherein

X represents, independently for each occurrence, O or S;

R, $R_1$, $R_2$, and $R_3$ represent, independently for each occurrence, H, alkyl, aryl, heteroalkyl, or heteroaryl;

$R_4$ represents alkyl, heteroalkyl, aryl, or heteroaryl;

$R_2$ is absent; and n is an integer selected from the range 0 to 2 inclusive.

13. A catalyst according to claim 12, wherein

X represents, independently for each occurrence, O or S;

R, $R_1$, $R_2$, and $R_3$ represent, independently for each occurrence, H, alkyl, aryl, heteroalkyl, or heteroaryl;

$R_4$ represents formyl or acyl;

$R_2$ is absent; and n is an integer selected from the range 0 to 2 inclusive.

* * * * *